(12) United States Patent
Igawa et al.

(10) Patent No.: US 8,288,017 B2
(45) Date of Patent: Oct. 16, 2012

(54) FUSED RING AROMATIC COMPOUND AND ORGANIC LIGHT-EMITTING DEVICE USING SAME

(75) Inventors: Satoshi Igawa, Fujisawa (JP); Masashi Hashimoto, Tokyo (JP); Shinjiro Okada, Kamakura (JP); Takao Takiguchi, Chofu (JP); Keiji Okinaka, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/092,340

(22) Filed: Apr. 22, 2011

(65) Prior Publication Data
US 2011/0204352 A1 Aug. 25, 2011

Related U.S. Application Data

(62) Division of application No. 12/305,318, filed as application No. PCT/JP2008/054222 on Mar. 3, 2008, now Pat. No. 7,960,041.

(30) Foreign Application Priority Data

Mar. 9, 2007 (JP) .................................. 2007-060609
Feb. 1, 2008 (JP) .................................. 2008-023231

(51) Int. Cl.
*H01L 51/54* (2006.01)
*C07C 13/62* (2006.01)

(52) U.S. Cl. .......... 428/690; 428/917; 585/27; 313/504; 313/506

(58) Field of Classification Search .................. None
See application file for complete search history.

(56) References Cited

U.S. PATENT DOCUMENTS 6,803,120 B2 10/2004 Fukuoka et al. ............ 428/690

7,960,041 B2 * 6/2011 Igawa et al. .................. 428/690
(Continued)

FOREIGN PATENT DOCUMENTS

JP 10-330295 12/1998
(Continued)

*Primary Examiner* — Dawn L. Garrett
(74) *Attorney, Agent, or Firm* — Fitzpatrick, Cella, Harper & Scinto

(57) ABSTRACT

There are provided a novel fused ring aromatic compound and an organic light-emitting device which has an optical output with extremely high efficiency and luminance, and also has extremely high durability. The organic light-emitting device includes an anode, a cathode, and a layer including an organic compound interposed between the anode and the cathode, wherein the layer comprises a fused ring aromatic compound represented by the general formula (I):

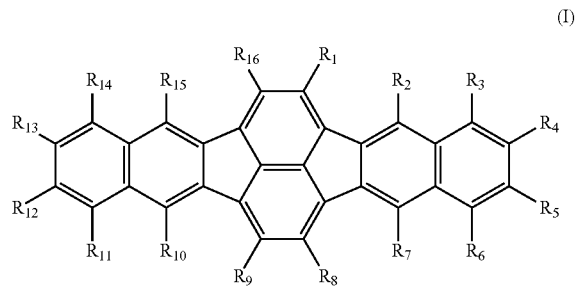

(I)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ each represent, independently of one another, a hydrogen atom, an alkyl group, a substituted or unsubstituted aralkyl group, a substituted or unsubstituted aryl group, a substituted or unsubstituted heterocyclic group, a substituted amino group, or a halogen atom.

7 Claims, 3 Drawing Sheets

U.S. PATENT DOCUMENTS

| | | | |
|---|---|---|---|
| 2003/0027016 A1 | 2/2003 | Ara et al. | 428/690 |
| 2004/0076853 A1 | 4/2004 | Jarikov | 428/690 |
| 2004/0232411 A1 | 11/2004 | Nakamura | 257/40 |
| 2006/0110623 A1 | 5/2006 | Funahashi et al. | 428/690 |
| 2007/0252141 A1 | 11/2007 | Negishi et al. | 257/40 |
| 2008/0272692 A1 | 11/2008 | Hashimoto et al. | 313/504 |
| 2008/0286611 A1 | 11/2008 | Muratsubaki et al. | 428/704 |
| 2009/0033210 A1 | 2/2009 | Saitoh et al. | 313/504 |
| 2009/0096368 A1 | 4/2009 | Kamatani et al. | 313/504 |
| 2009/0121625 A1 | 5/2009 | Ohrui et al. | 313/504 |
| 2009/0278446 A1* | 11/2009 | Igawa et al. | 313/504 |

FOREIGN PATENT DOCUMENTS

| | | |
|---|---|---|
| JP | 11-176573 | 7/1999 |
| JP | 2001-160489 | 6/2001 |
| JP | 2002-008867 | 1/2002 |
| JP | 2002-110356 | 4/2002 |
| JP | 2002-170681 | 6/2002 |
| JP | 2003-212875 | 7/2003 |
| JP | 2004-349319 | 12/2004 |

* cited by examiner

FUSED RING AROMATIC COMPOUND AND ORGANIC LIGHT-EMITTING DEVICE USING SAME

CROSS-REFERENCE TO RELATED APPLICATIONS

This application is a divisional application of U.S. application Ser. No. 12/305,318, filed Dec. 17, 2008, which is a National Stage Entry of International Application No. PCT/JP2008/054222, filed on Mar. 3, 2008. The contents of the aforementioned applications are incorporated herein by reference in their entireties.

TECHNICAL FIELD

The present invention relates to a fused ring aromatic compound and an organic light-emitting device using the compound.

BACKGROUND ART

An organic light-emitting device is a device having a thin film which contains a fluorescent or phosphorescent organic compound and is interposed between an anode and a cathode. Electrons and holes (positive holes) are injected from the respective electrodes, whereby excitons of the fluorescent or phosphorescent compound are produced. The excitons radiate light upon return thereof to a ground state. Recent progress of an organic light-emitting device is remarkable, and the characteristics of the device enable a thin and light weight light-emitting device with a high luminance at a low applied voltage, a variety of emission wavelengths, and a high-speed responsibility. From this fact, it is suggested that the device have potential to find use in a wide variety of applications.

However, in the present circumstances, an optical output with a higher luminance or a higher conversion efficiency is needed. In addition, the organic light-emitting device still involves a large number of problems in terms of durability such as a change over time due to long-term use and degradation due to an atmospheric gas containing oxygen, moisture or the like. Further, when the application of the device to a full-color display or the like is taken into consideration, the emission of blue, green, or red light with good color purity is needed. However, these problems have not been sufficiently solved yet.

In order to solve the problems, there has been proposed incorporation, as a material for an organic light-emitting device, of a relatively large fused ring aromatic compound containing a pentacyclic structure. Specific examples of the relatively large fused ring aromatic compound containing a pentacyclic structure and an organic light-emitting device using the compound are disclosed in Japanese Patent Application Laid-Open Nos. H10-330295, 2002-170681, 2002-110356, H11-176573, and 2002-008867.

DISCLOSURE OF THE INVENTION

It is an object of the present invention is to provide a novel fused ring aromatic compound.
It is another object of the present invention is to provide an organic light-emitting device which has an optical output with extremely high efficiency and luminance, and also has extremely high durability.

Further, it is still another object of the present invention is to provide an organic light-emitting device that can be easily produced at a relatively low cost.

The above objects are achieved by the present invention described below.

That is, according to an aspect of the present invention, there is provided a fused ring aromatic compound represented by the following general formula (I):

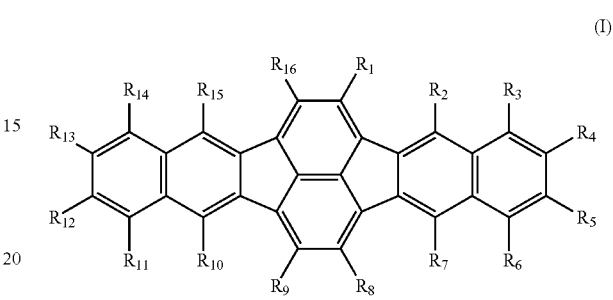

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ each represent, independently of one another, a hydrogen atom, an alkyl group, a substituted or unsubstituted aralkyl group, a substituted or unsubstituted aryl group, a substituted or unsubstituted heterocyclic group, a substituted amino group, or a halogen atom, provided that at least one of combinations of $R_1$ and $R_9$, $R_2$ and $R_{10}$, $R_3$ and $R_{11}$, $R_4$ and $R_{12}$, $R_5$ and $R_{13}$, $R_6$ and $R_{14}$, $R_7$ and $R_{15}$, and $R_8$ and $R_{16}$, is a combination of different substituents.

In the present invention, it is preferred that $R_2$, $R_7$, $R_{10}$, and $R_{15}$ each represent a substituted or unsubstituted aryl group.

According to another aspect of the present invention, there is provided an organic light-emitting device which includes an anode, a cathode, and a layer including an organic compound interposed between the anode and the cathode, in which the layer includes the above-mentioned fused ring aromatic compound.

In the present invention, it is preferred that the layer is a light-emitting layer.

Further, it is preferred that the light-emitting layer includes a host and a guest and the guest includes the fused ring aromatic compound.

Moreover, it is preferred that the organic light-emitting device is an electroluminescent device that emits light by applying a voltage between an anode and a cathode.

According to the present invention, there can be provided a novel fused ring aromatic compound.

Further, according to the present invention, there can be provided an organic light-emitting device which has an optical output with extremely high efficiency and luminance, and also has extremely high durability.

Moreover, the organic light-emitting device of the present invention can be produced by using a vacuum evaporation method, a casting method, or the like, and can be easily produced so as to have a large area at a relatively low cost.

BEST MODE FOR CARRYING OUT THE INVENTION

Figure 1:
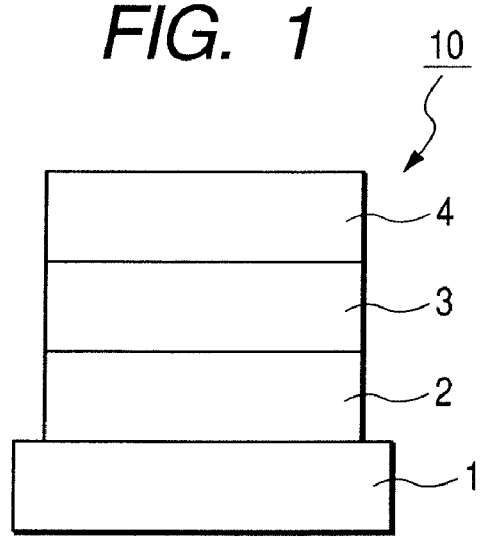
FIG. 1 is a cross-sectional view illustrating a first embodiment of the organic light-emitting device of the present invention.

The present invention will be described below in detail. Firstly, the fused ring aromatic compound of the present invention will be described.

The fused ring aromatic compound of the present invention is represented by the following general formula (I):

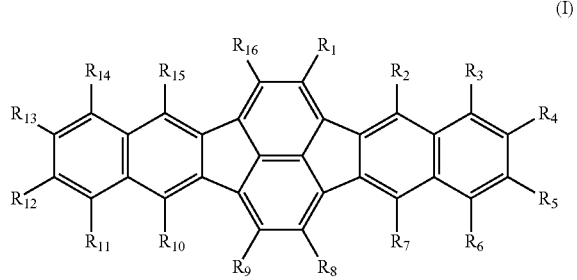

(I)

In the formula (I), $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ each represent, independently of one another, a hydrogen atom, an alkyl group, a substituted or unsubstituted aralkyl group, a substituted or unsubstituted aryl group, a substituted or unsubstituted heterocyclic group, a substituted amino group, or a halogen atom, provided that at least one of combinations of $R_1$ and $R_9$, $R_2$ and $R_{10}$, $R_3$ and $R_{11}$, $R_4$ and $R_{12}$, $R_5$ and $R_{13}$, $R_6$ and $R_{14}$, $R_7$ and $R_{15}$, and $R_8$ and $R_{16}$, is a combination of different substituents.

Examples of the alkyl groups representing $R_1$ to $R_{16}$ include, but not limited to, a methyl group, an ethyl group, a normal propyl group, an isopropyl group, a normal butyl group, a tertiary butyl group, an octyl group, a cyclohexyl group, and a trifluoromethyl group.

Examples of the aralkyl groups representing $R_1$ to $R_{16}$ include, but not limited to, a benzyl group and a phenethyl group.

Examples of the aryl groups representing $R_1$ to $R_{16}$ include, but not limited to, a phenyl group, a biphenyl group, a terphenyl group, fluorenyl group, a naphthyl group, a fluoranthenyl group, an anthryl group, a phenanthryl group, a pyrenyl group, a tetracenyl group, a pentacenyl group, a triphenylenyl group, and a perylenyl group.

Examples of the heterocyclic groups representing $R_1$ to $R_{16}$ include, but not limited to, a thienyl group, a pyrrolyl group, a pyridyl group, an oxazolyl group, an oxadiazolyl group, a thiazolyl group, a thiadiazolyl group, a terthienyl group, a quinolyl group, an isoquinolyl group, and a carbazolyl group.

Examples of the substituted amino groups representing $R_1$ to $R_{16}$ include, but not limited to, a dimethylamino group, a diethylamino group, a dibenzylamino group, a diphenylamino group, a ditolylamino group, and a dianisolylamino group.

Examples of the halogen atoms representing $R_1$ to $R_{16}$ include fluorine, chlorine, bromine and iodine.

Examples of substituents which the aralkyl group, the aryl group and the heterocyclic group may have include, but not limited to, alkyl groups such as a methyl group, an ethyl group, a propyl group, an isopropyl group, a tertiary butyl group and a cyclohexyl group, aralkyl groups such as a benzyl group and a phenethyl group, aryl groups such as a phenyl group and a biphenyl group, heterocyclic groups such as a thienyl group, a pyrrolyl group and a pyridyl group, substituted amino groups such as a dimethylamino group, a diethylamino group, a dibenzylamino group, a diphenylamino group, a ditolylamino group, and a dianisoylamino group, alkoxyl groups such as a methoxyl group, an ethoxyl group and a propoxyl group, aryloxyl groups such as phenoxyl group, halogen atoms such as fluorine, chlorine, bromine and iodine, and cyano group.

Further, since the fused ring aromatic compound of the present invention has a relative large fused ring in itself, when it is used as a light-emitting material for an organic light-emitting device, it is necessary to consider concentration quenching of the light-emitting material due to an interaction of fused rings. Therefore, it is effective for suppressing concentration quenching in the organic light-emitting device that molecular symmetry is reduced and association property of molecules are reduced. Accordingly, in order to reduce the molecular symmetry, it is important that at least one of combinations of substituents located at positions in point symmetry about position of the center of the molecular skeleton, is a combination of different substituents. The expression "combinations of substituents located at positions in point symmetry about position of center of molecular skeleton" herein employed refers to, for example, combinations of $R_1$ and $R_9$, $R_2$ and $R_{10}$, $R_3$ and $R_{11}$, $R_4$ and $R_{12}$, $R_5$ and $R_{13}$, $R_6$ and $R_{14}$, $R_7$ and $R_{15}$, and $R_8$ and $R_{16}$ in the compound of the formula (I).

Further, in order to suppress concentration quenching of a light-emitting material, it is preferable to incorporate a substituent having large steric hindrance. For example, it is effective to incorporate a tertiary butyl group or the like.

Further, by reducing the molecular symmetry and lowering the crystallinity, the sublimation temperature and the evaporation temperature can be decreased to improve the sublimation and evaporation rates, so that the productivity of the compound and the organic light-emitting device can be expected to be improved.

The method of producing the fused ring aromatic compound represented by the general formula (I) is not particularly limited, but the fused ring aromatic compound can be produced according to the production method shown below, for example.

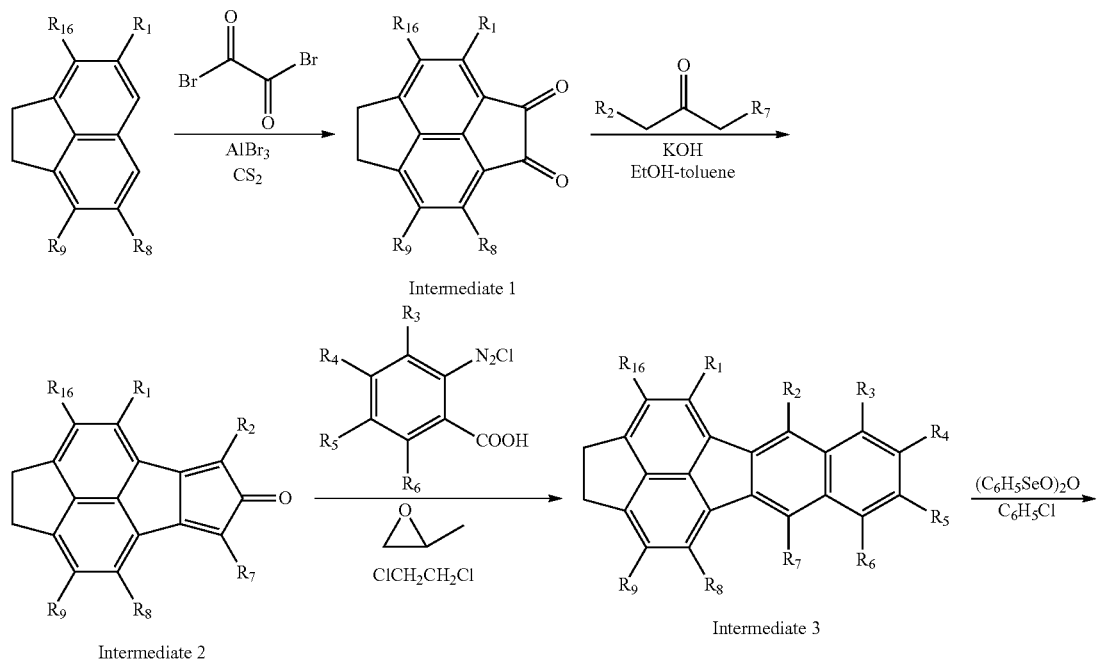
Intermediate 1
Intermediate 2
Intermediate 3
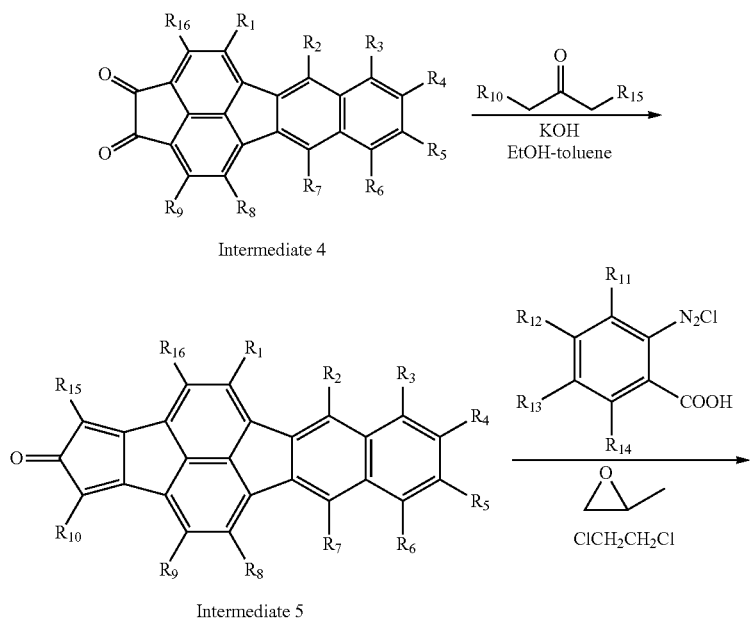
Intermediate 4
Intermediate 5
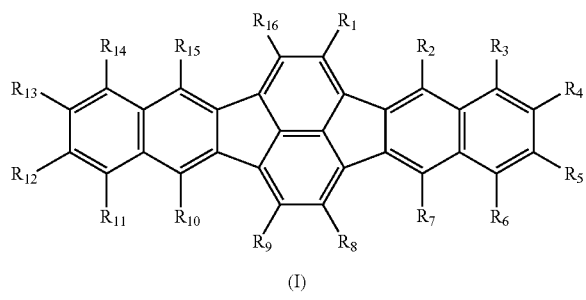
(I)

When the fused ring aromatic compound of the present invention is produced according to the above-mentioned production method, $R_2$, $R_7$, $R_{10}$, and $R_{15}$ in the formula (I) are each preferably a substituted or unsubstituted aryl group from the viewpoint of stability of the intermediate 2 and the intermediate 5 above.

Hereinafter, specific structural formulas of the fused ring aromatic compounds of the present invention are represented below. However, these structural formulas represent only typical examples and the present invention should not be limited thereto.

A-1
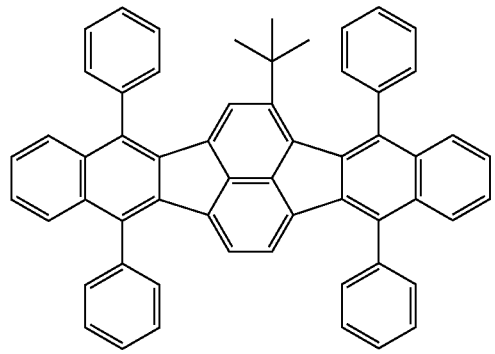

A-2
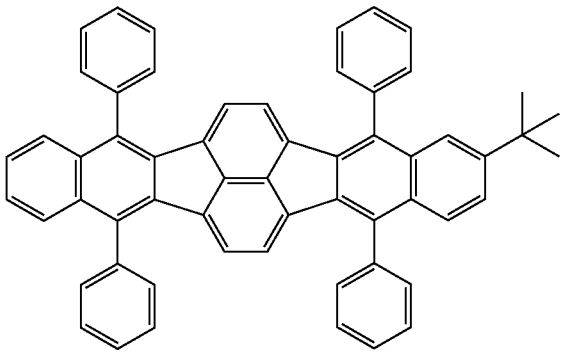

A-3
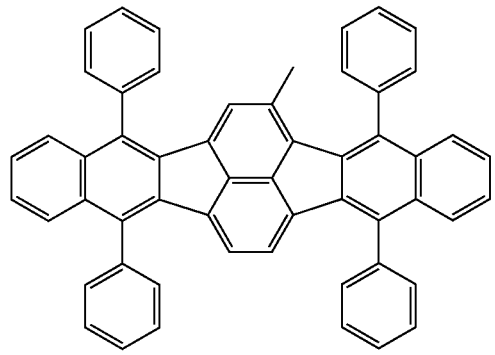

A-4
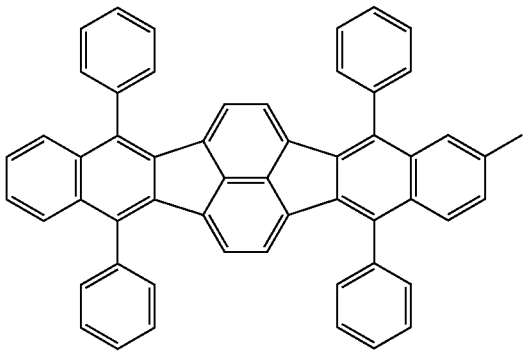

A-5
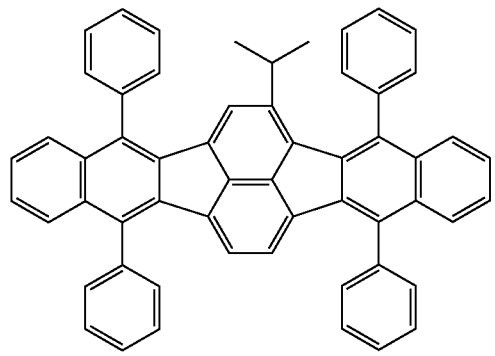

A-6
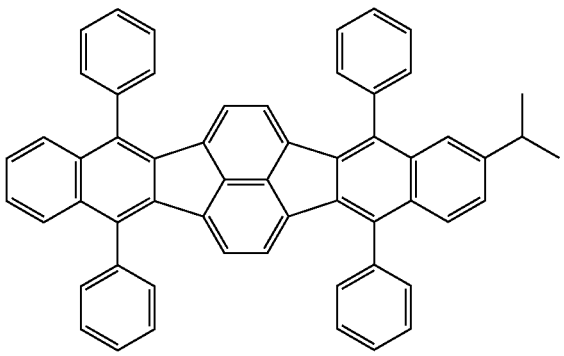

A-7
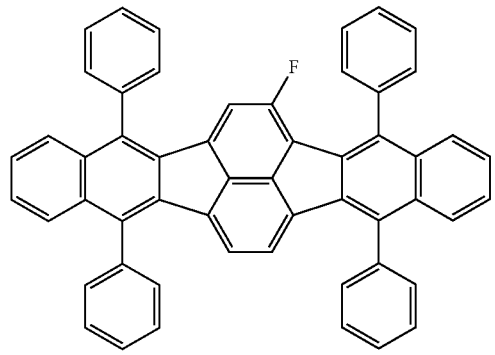

A-8
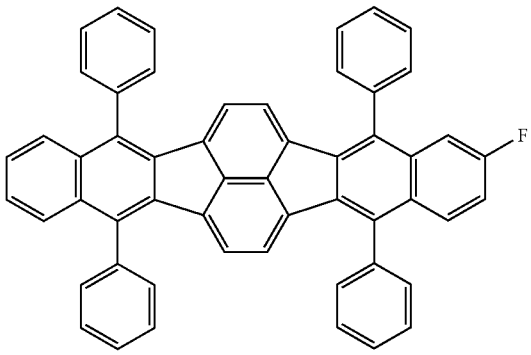

-continued
A-9
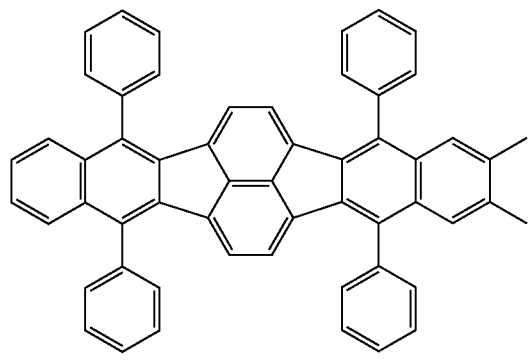
A-10
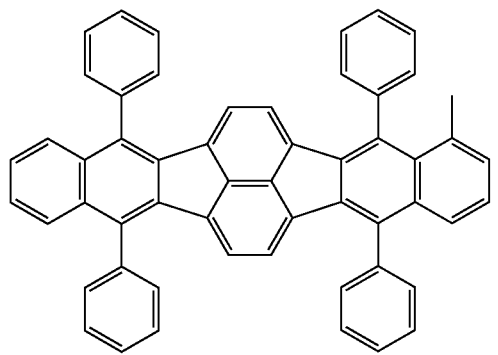
A-11
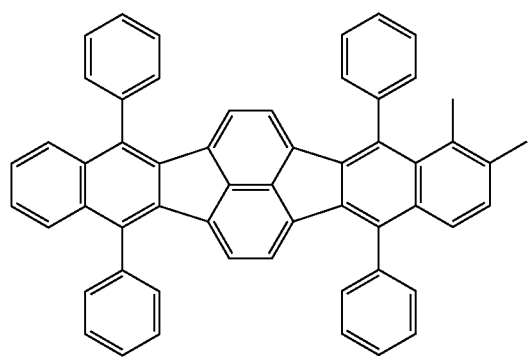
A-12
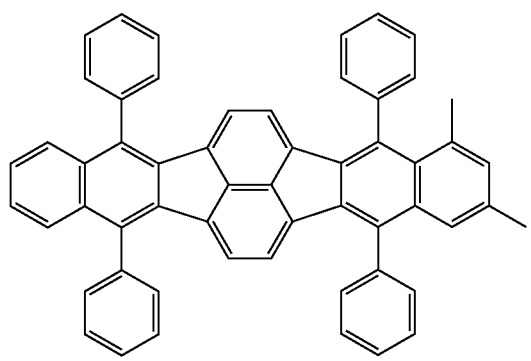
A-13
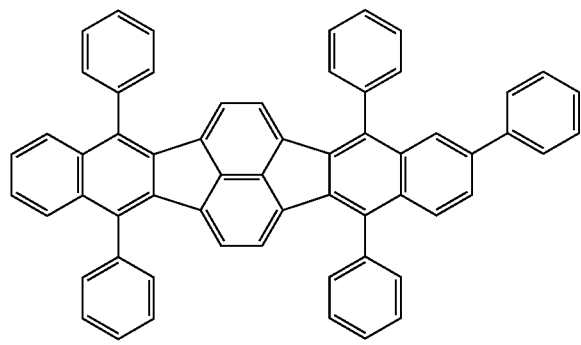
A-14
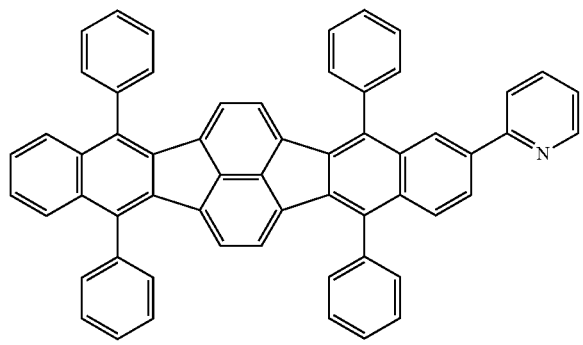
A-15
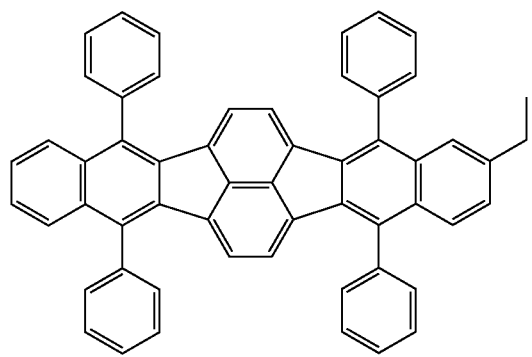
A-16
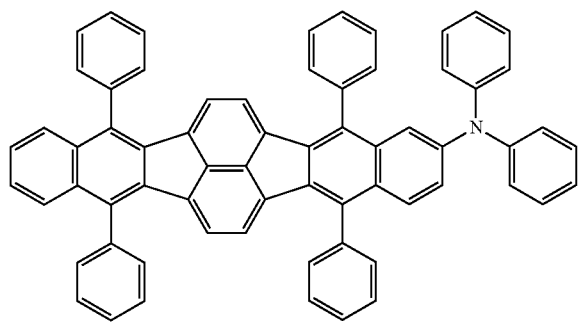

-continued
A-17
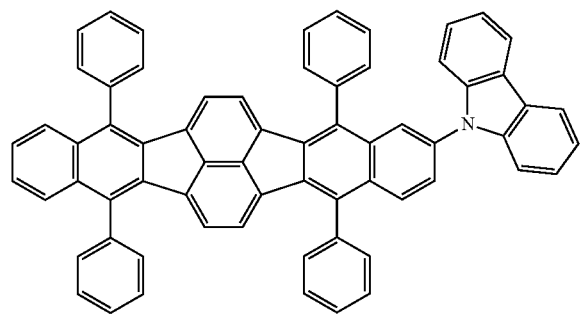
A-18
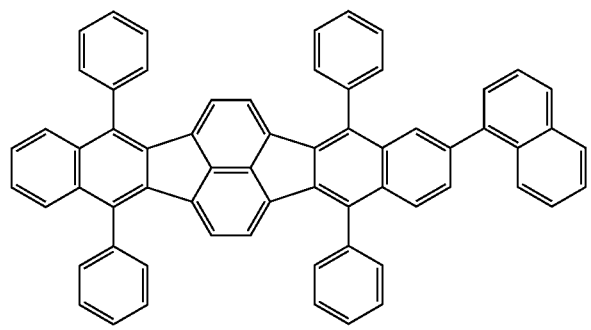
A-19
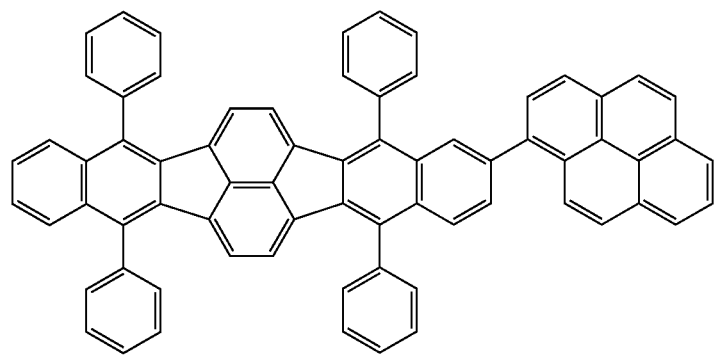
A-20
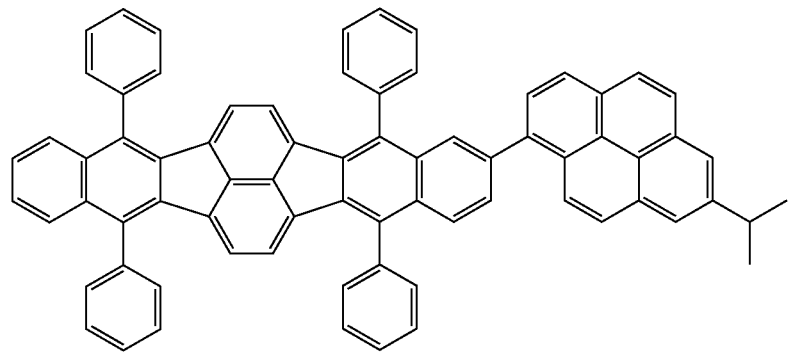
A-21
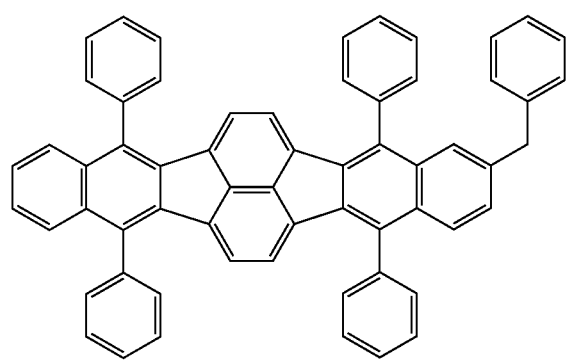
A-22
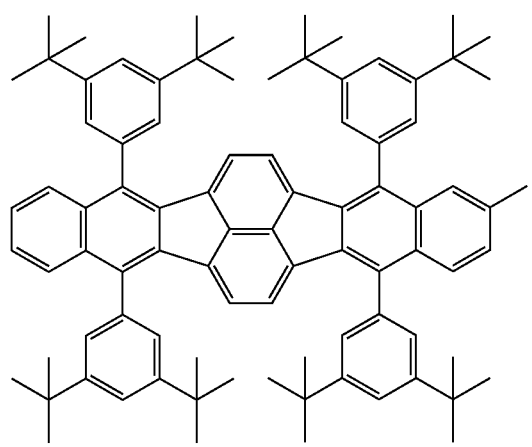

-continued
A-23
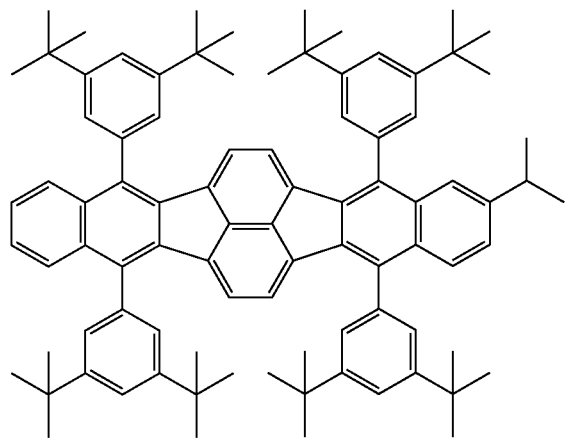
A-24
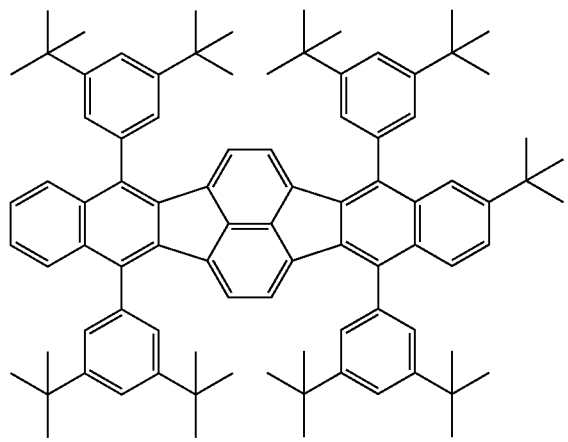
A-25
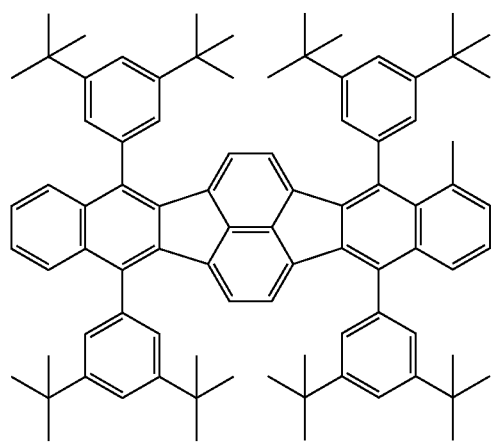
A-26
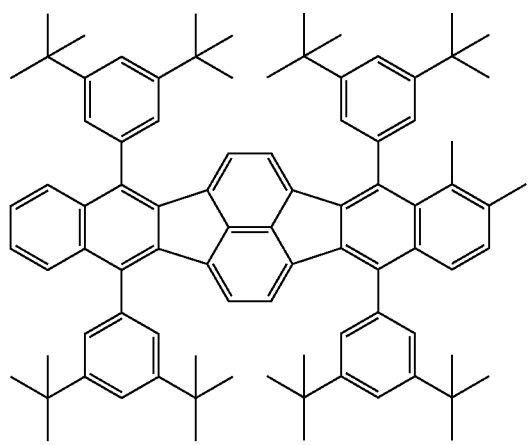
A-27
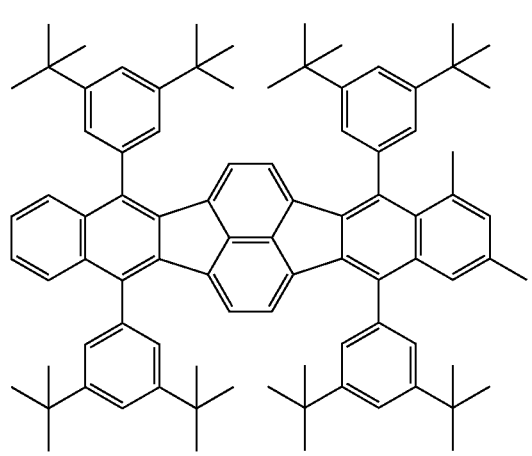
A-28
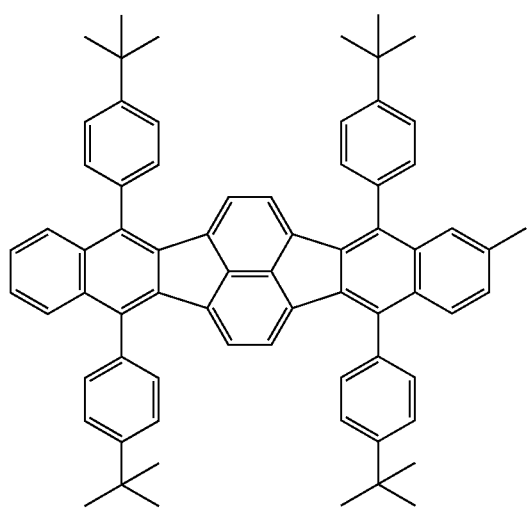

-continued
A-29
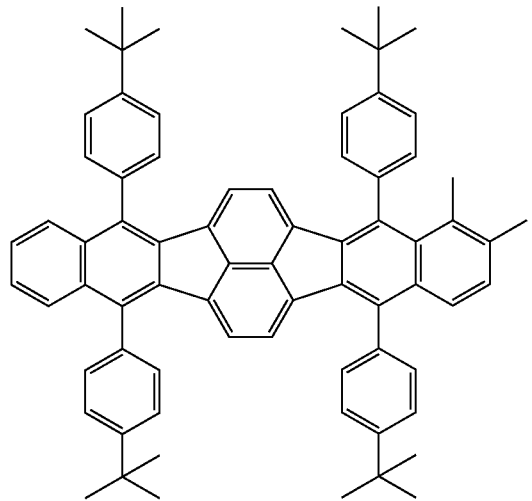
A-30
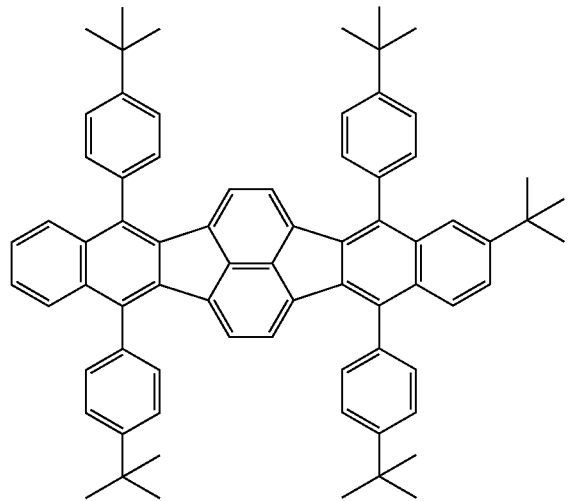
A-31
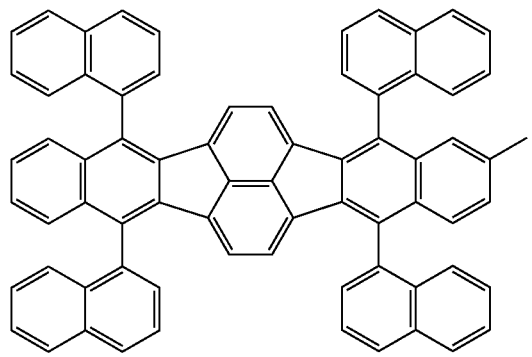
A-32
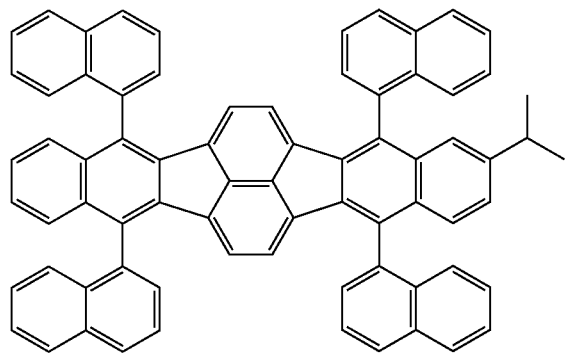
A-33
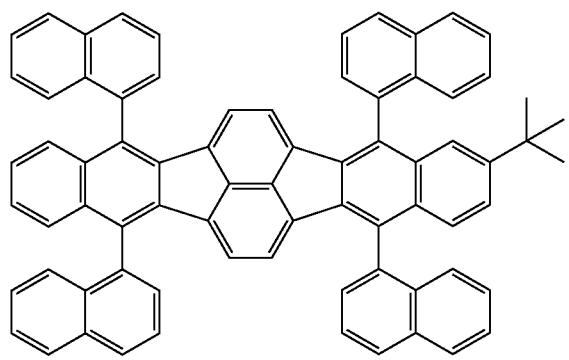
A-34
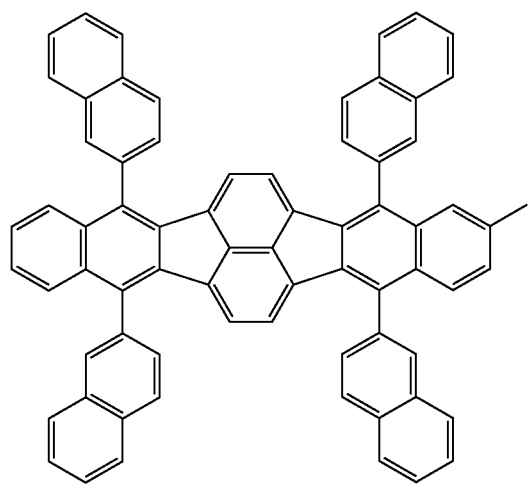

-continued
A-35
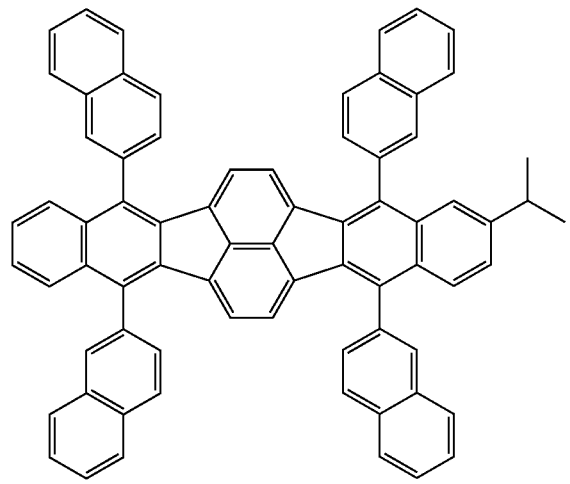
A-36
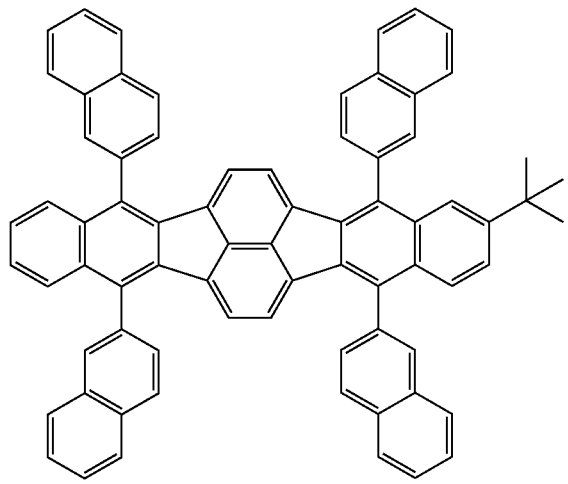
A-37
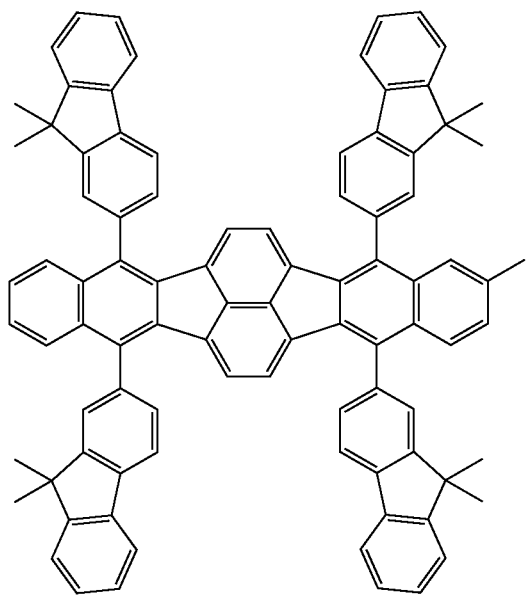
A-38
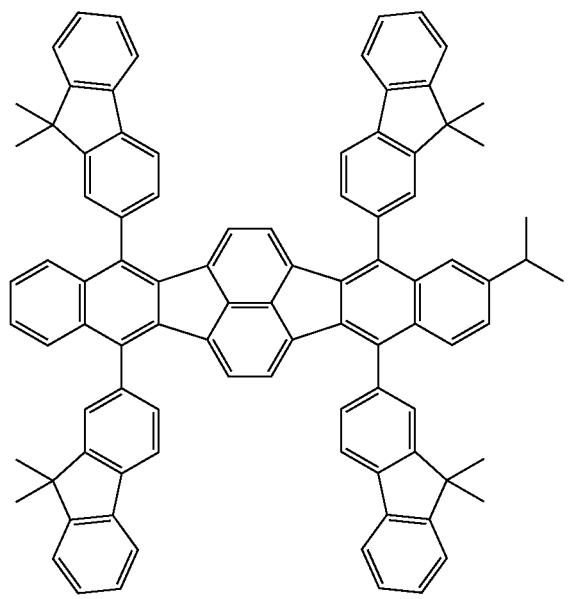

-continued
A-39
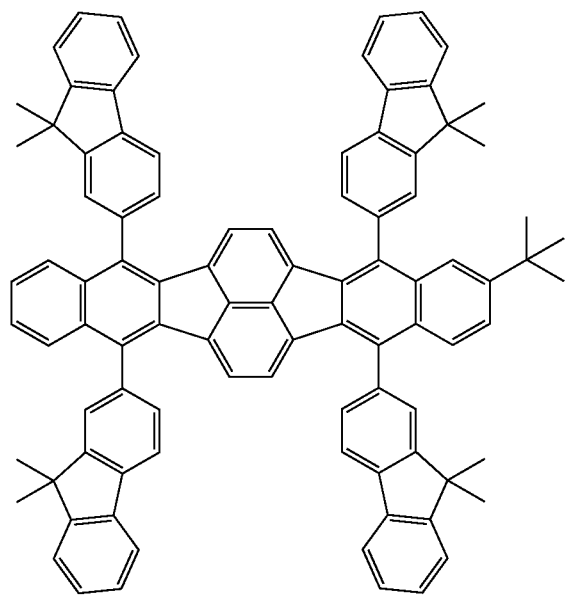
A-40
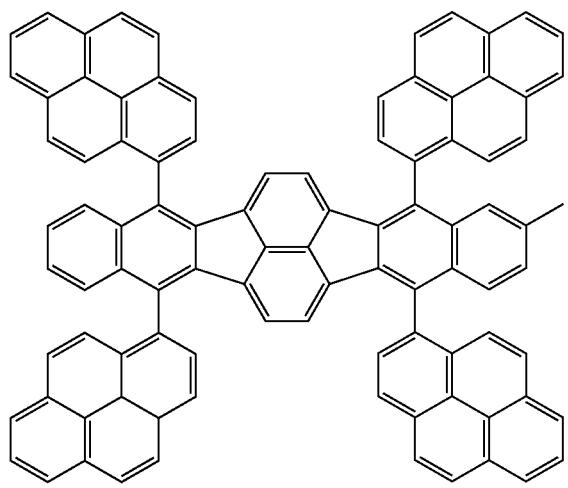
A-41
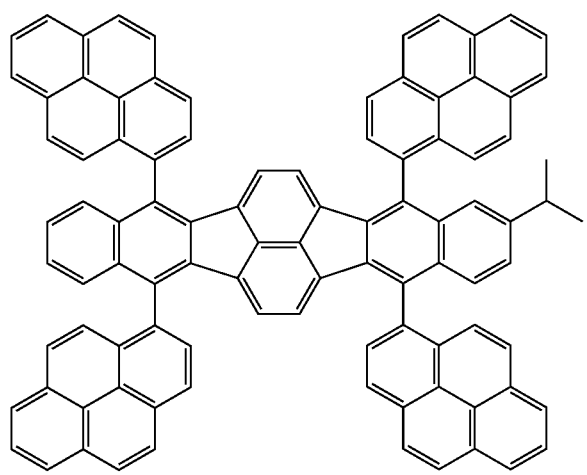
A-42
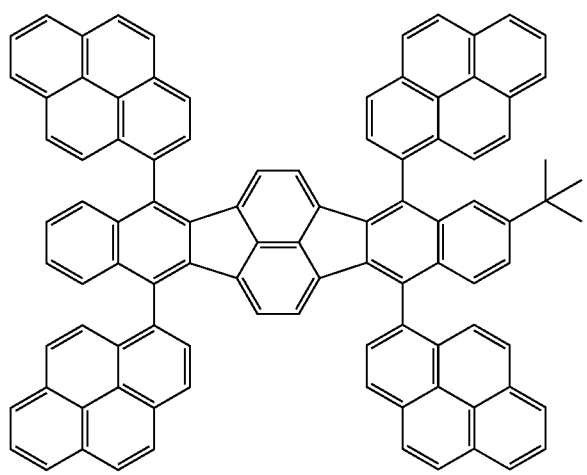

-continued
B-1
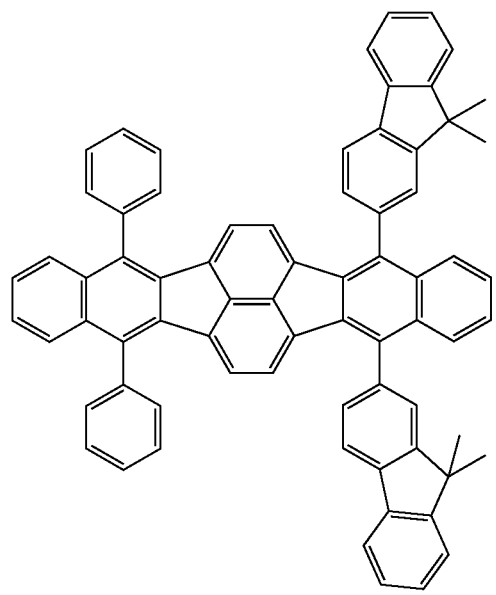
B-2
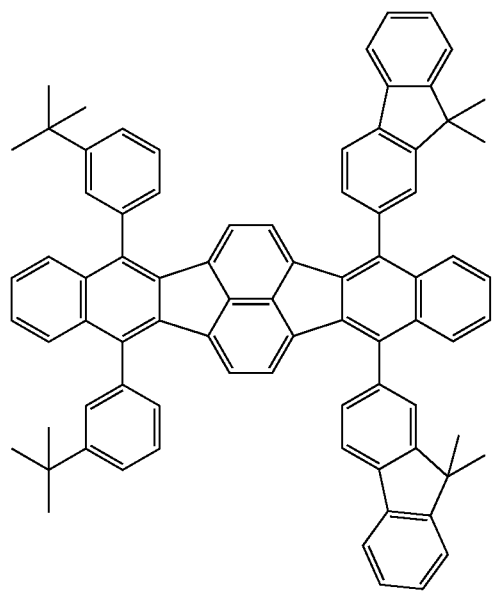
B-3
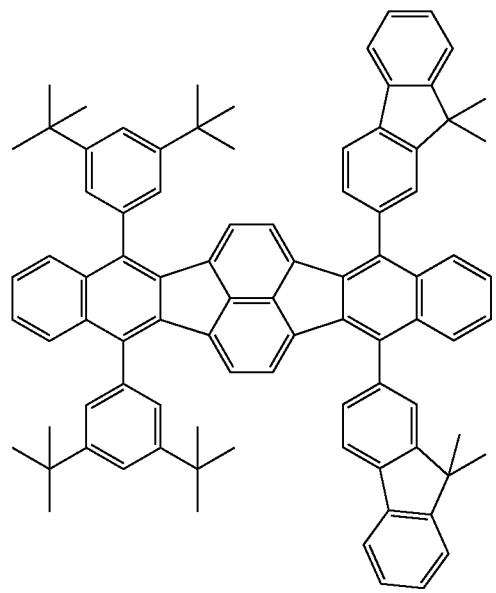
B-4
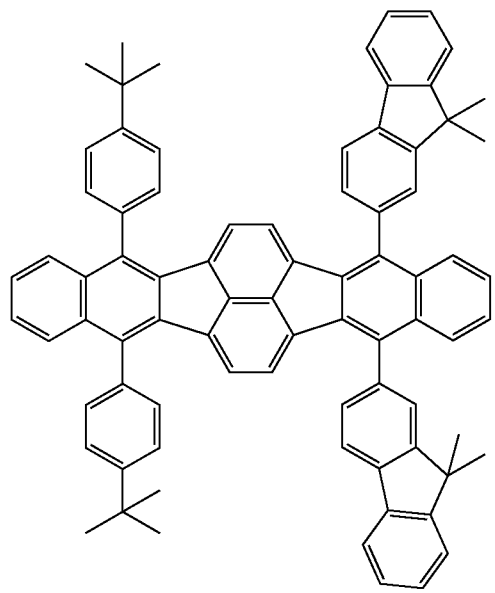

-continued
B-5
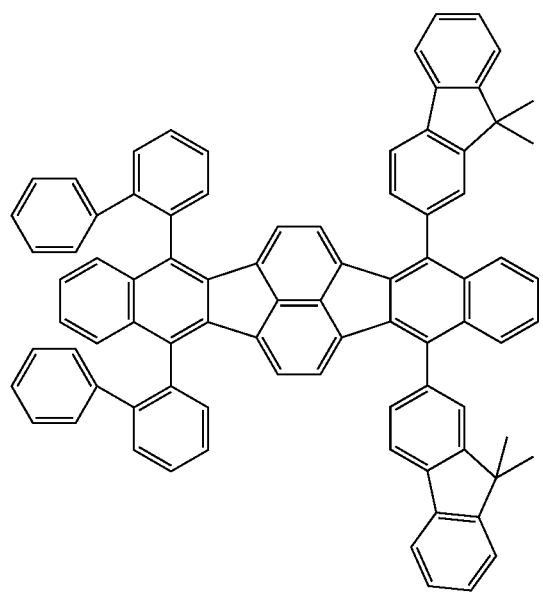
B-6
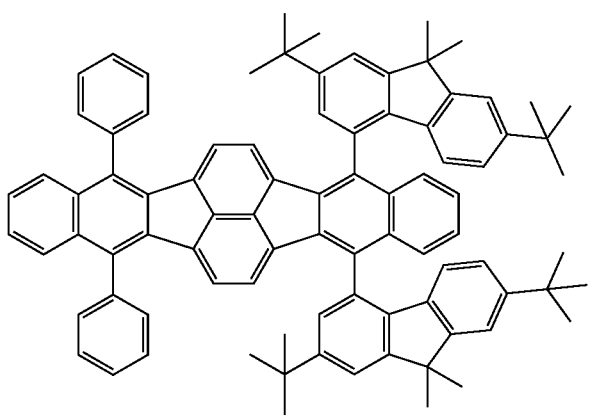
B-7
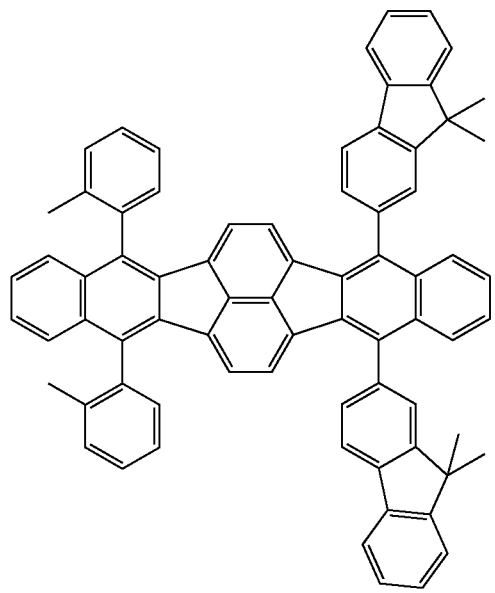
B-8
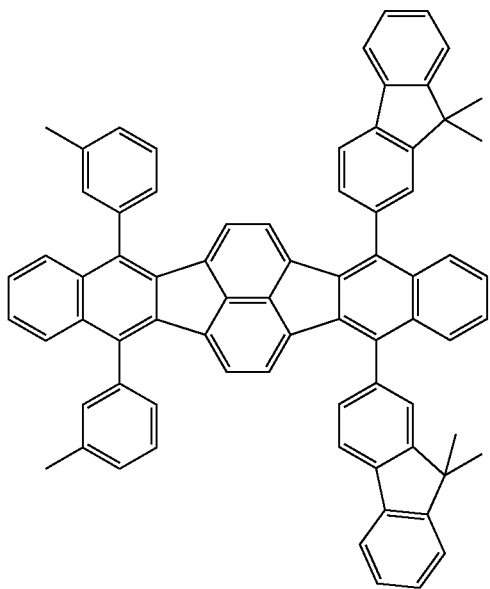

-continued
B-9
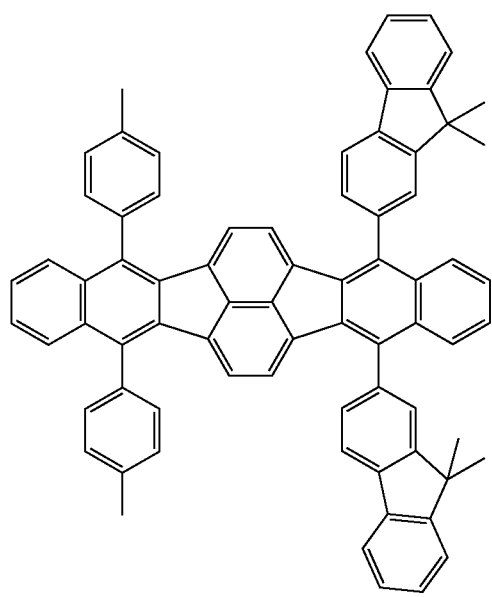
B-10
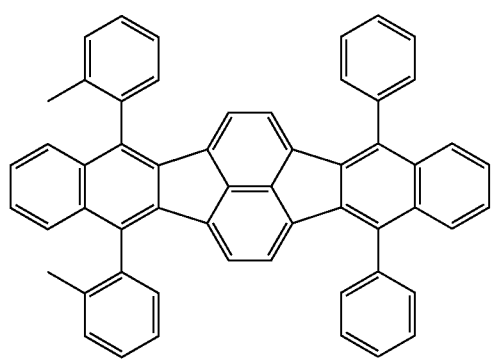
B-11
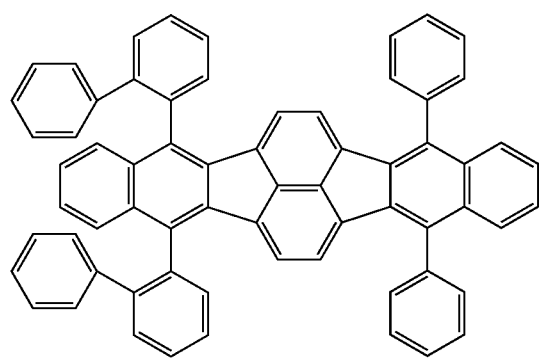
B-12
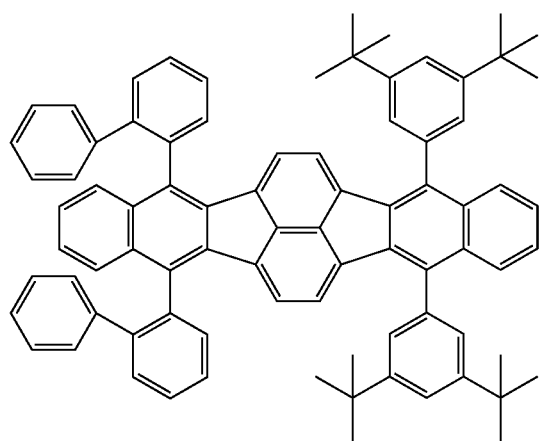
B-13
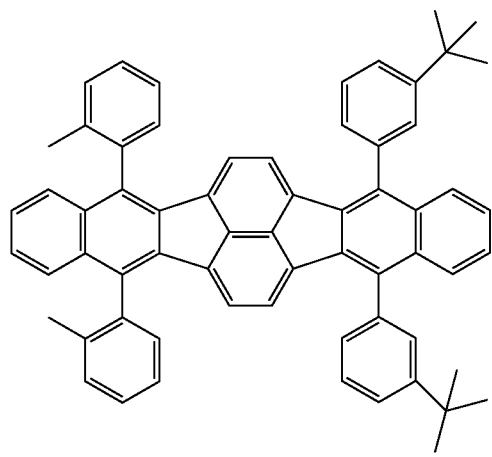
B-14
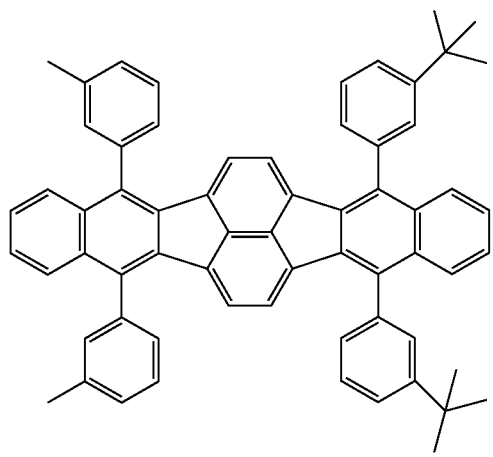

-continued
B-15
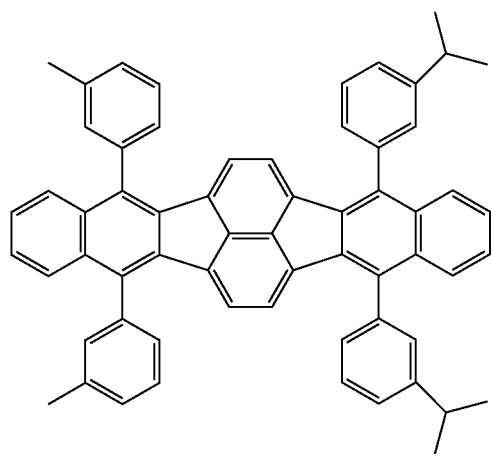
B-16
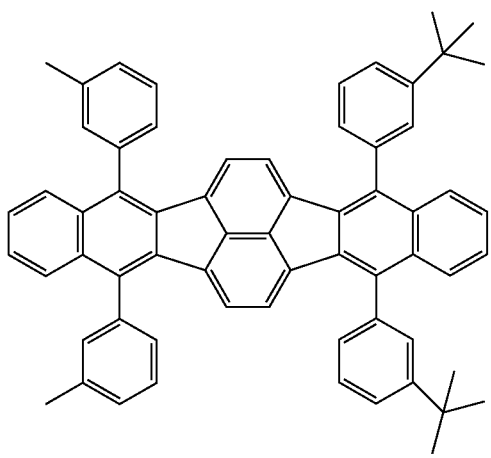
B-17
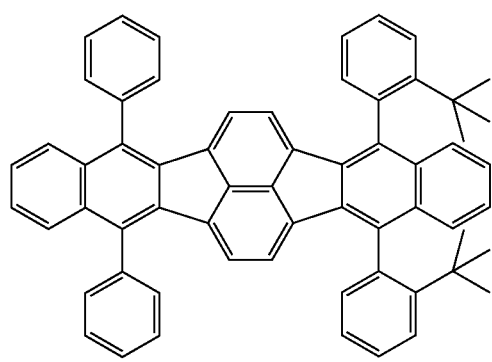
B-18
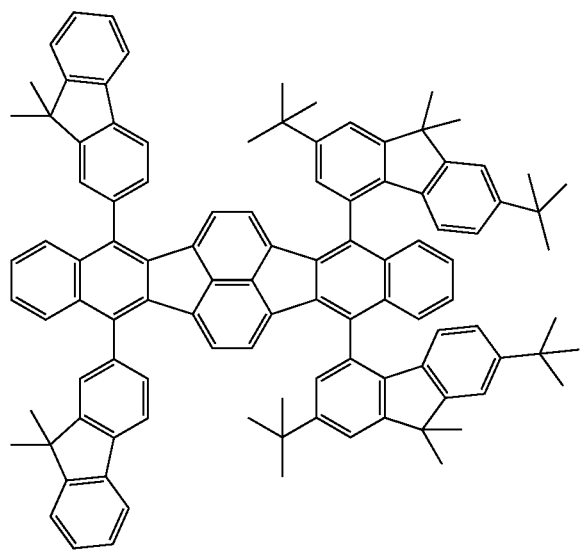
B-19
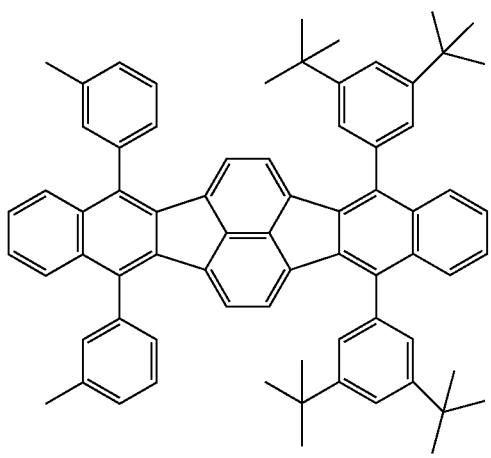

B-20
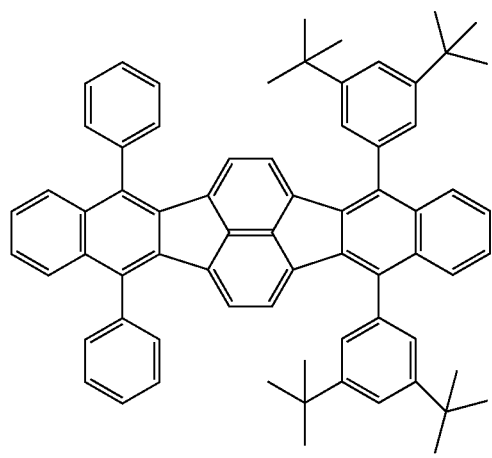
B-21
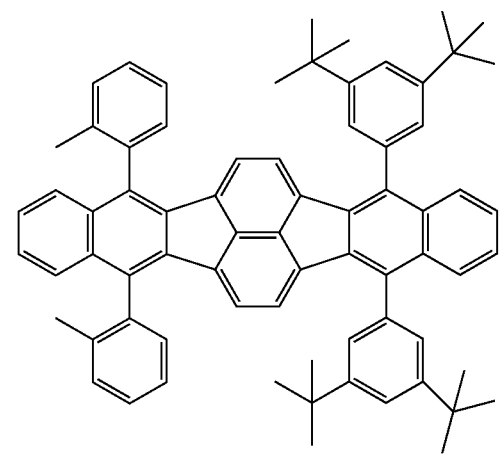
B-22
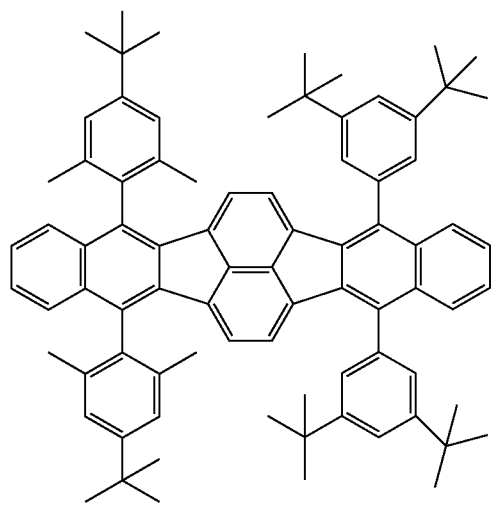
B-23
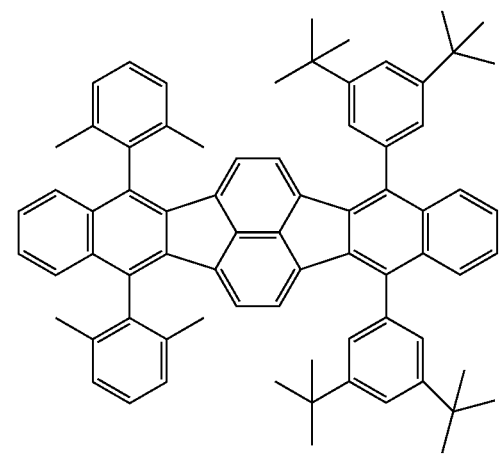
B-24
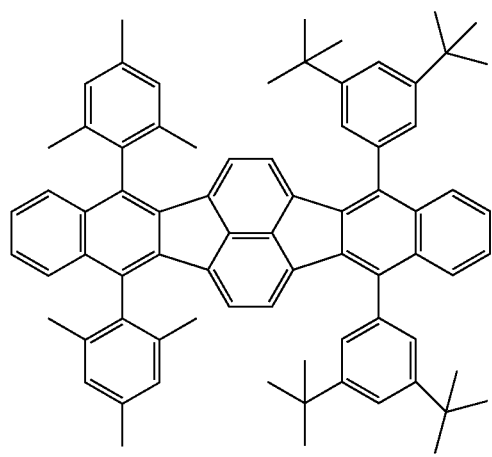
B-25
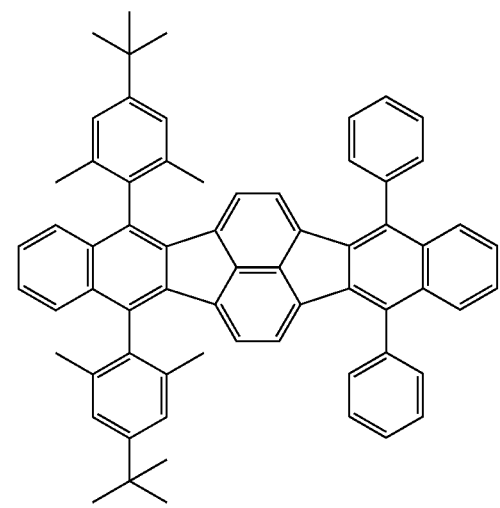

-continued
B-26
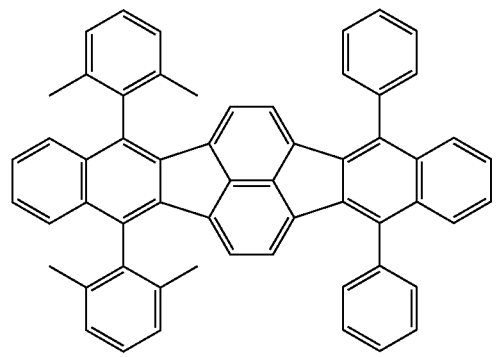
B-27
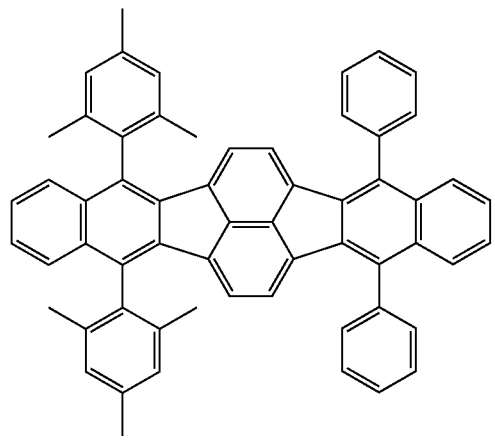
C-1
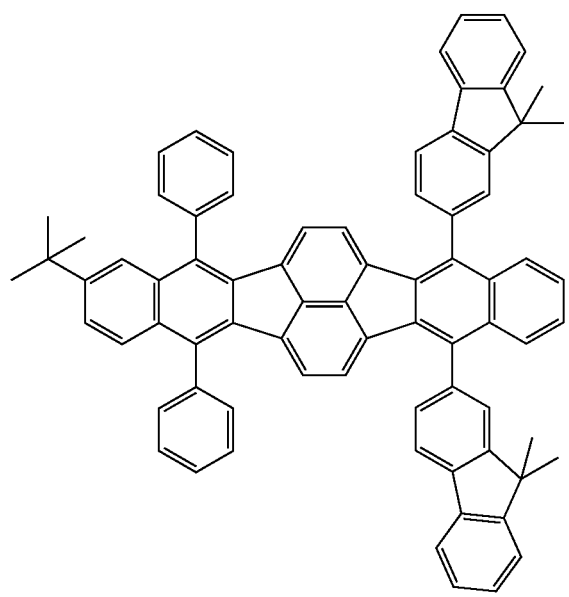
C-2
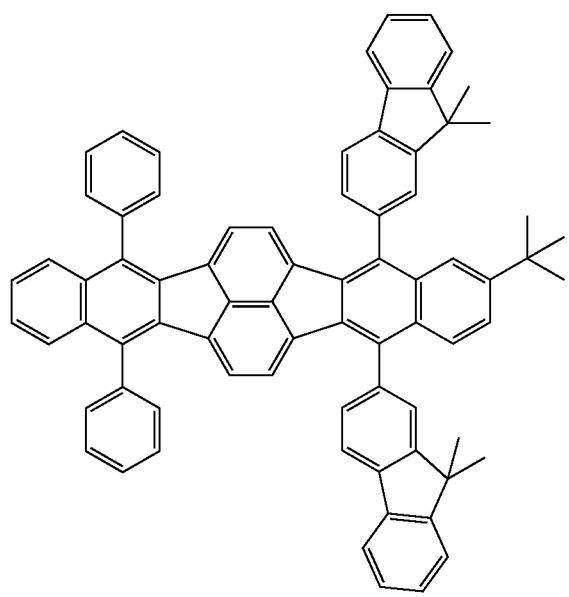
C-3
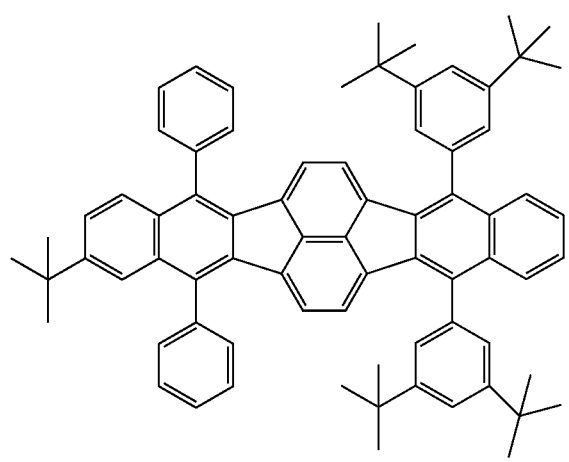
C-4
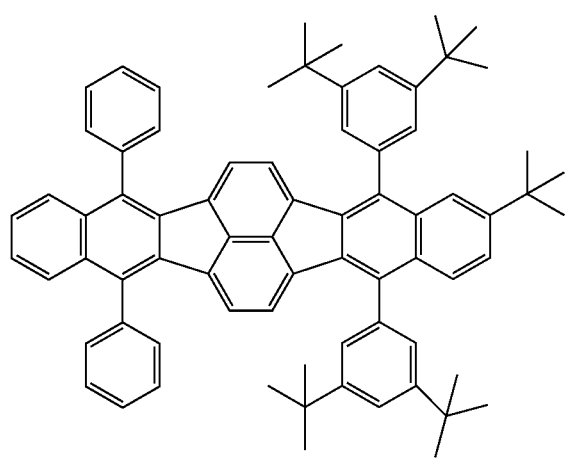

-continued
C-5
C-6
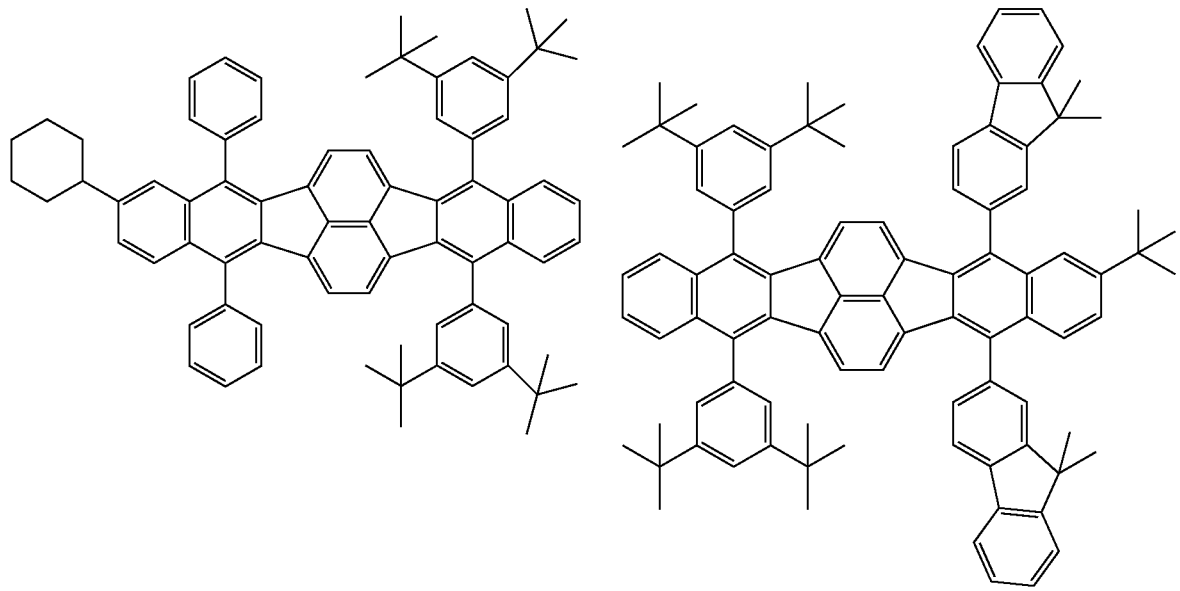
C-7
C-8
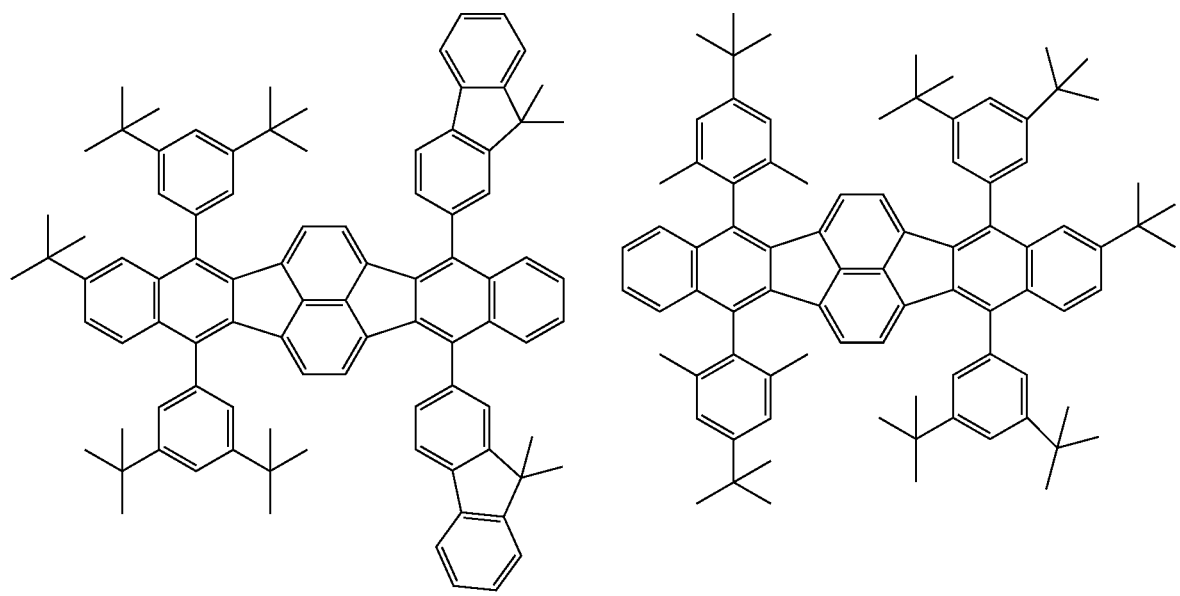

-continued
C-9
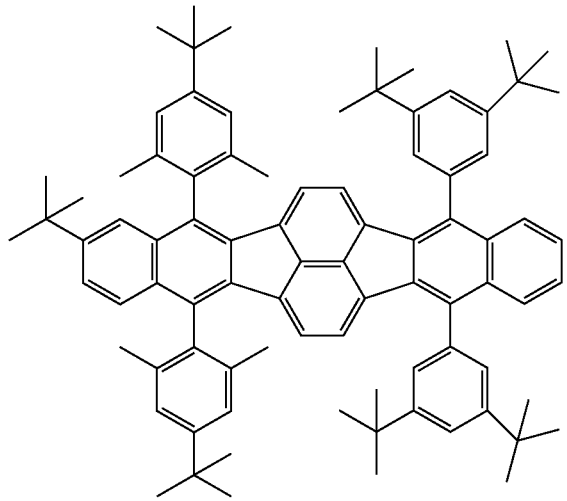
C-10
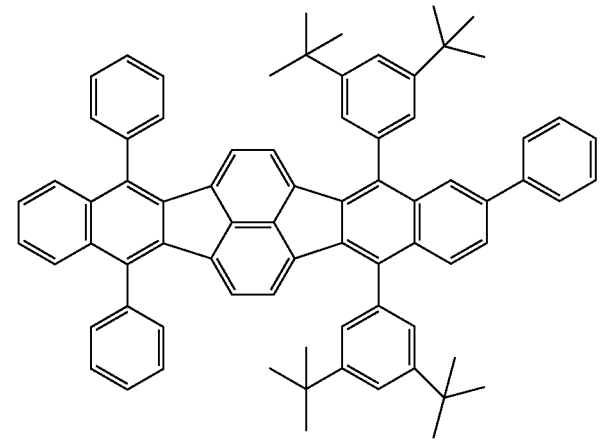
C-11
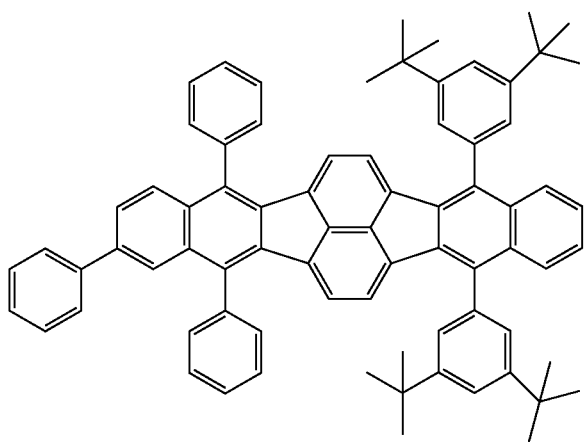
C-12
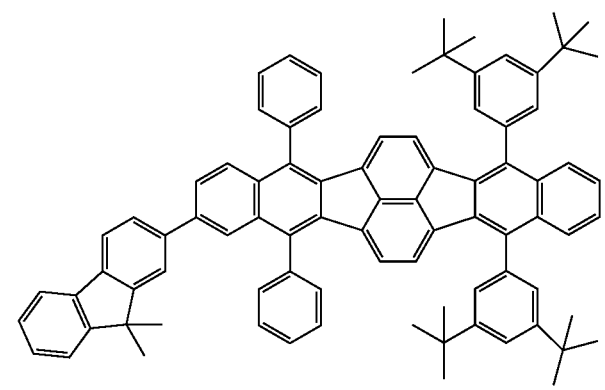
D-1
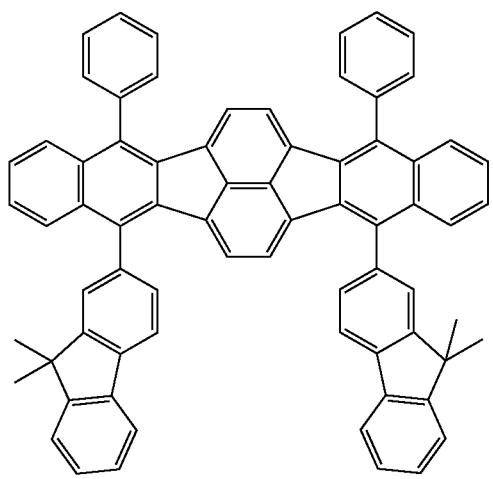
D-2
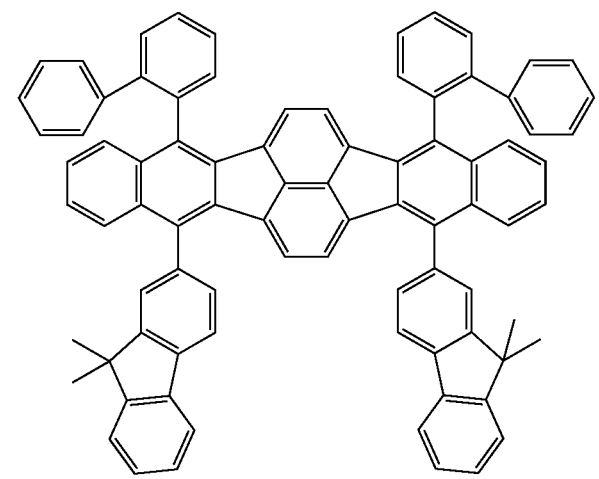

-continued

D-3
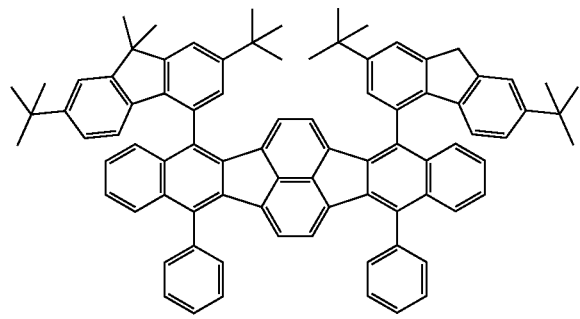

D-4
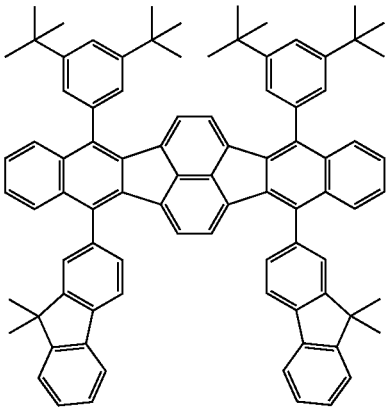

D-5
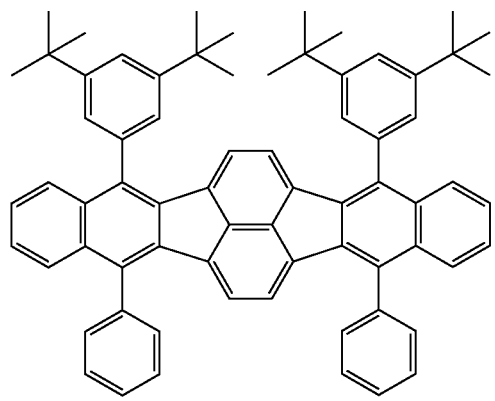

D-6
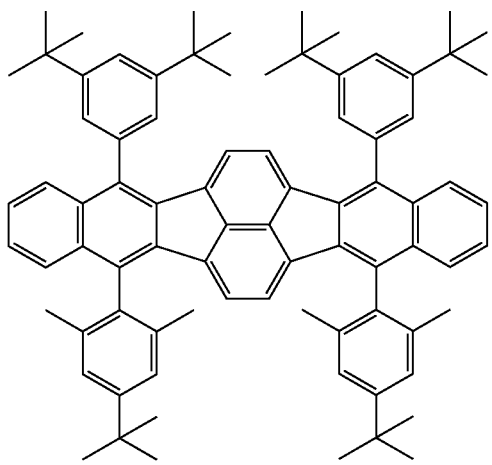

Next, the organic light-emitting device of the present invention will be described in detail.

The organic light-emitting device of the present invention is formed of an anode, a cathode, and a layer formed of an organic compound and interposed between the anode and the cathode. The layer formed of the organic compound contains the fused ring aromatic compound of the present invention. The organic light-emitting device of the present invention is preferably an electroluminescent device that emits light by applying a voltage between an anode and a cathode.

Hereinafter, the organic light-emitting device of the present invention will be described in detail with reference to the drawings.

First, reference numerals used in the figures will be described. Reference numeral 1 denotes a substrate, reference numeral 2 denotes an anode, reference numeral 3 denotes a light-emitting layer, reference numeral 4 denotes a cathode, reference numeral 5 denotes a hole-transporting layer, reference numeral 6 denotes an electron-transporting layer, reference numeral 7 denotes a hole injection layer, reference numeral 8 denotes a hole/exciton blocking layer, and reference numerals 10, 20, 30, 40, 50, and 60 each denote an organic light-emitting device.

FIG. 1 is a schematic cross-sectional view illustrating a first embodiment of the organic light-emitting device of the present invention. In the organic light-emitting device 10 shown in FIG. 1, there are sequentially provided on a substrate 1, an anode 2, a light-emitting layer 3 and a cathode 4.

The configuration of the organic light-emitting device 10 is useful when the light-emitting layer 3 is composed of a compound having all of hole transporting ability, electron transporting ability and light emitting ability. Further, the configuration is also useful when the light-emitting layer 3 is composed of a mixture of compounds having the characteristics of any one of hole transporting ability, electron transporting ability, and light emitting ability.

Figure 2:
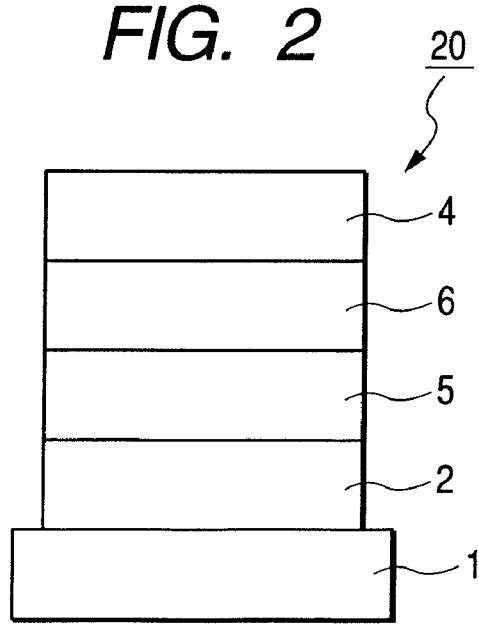
FIG. 2 is a cross-sectional view illustrating a second embodiment of the organic light-emitting device of the present invention.

FIG. 2 is a schematic cross-sectional view illustrating a second embodiment of the organic light-emitting device of the present invention. In the organic light-emitting device 20 shown in FIG. 2, there are sequentially provided on a substrate 1, an anode 2, a hole-transporting layer 5, an electron-transporting layer 6, and a cathode 4. The configuration of the organic light-emitting device 20 is useful when an organic compound having either one of hole transporting ability and electron transporting ability and an organic compound having only electron transporting ability or hole transporting ability are used in combination. Incidentally, in the organic light-emitting device 20 shown in FIG. 2, the hole-transporting layer 5 and the electron-transporting layer 6 each serve also as a light-emitting layer.

Figure 3:
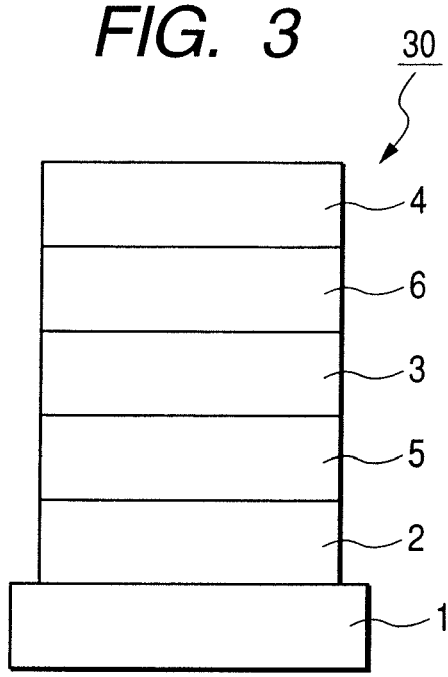
FIG. 3 is a cross-sectional view illustrating a third embodiment of the organic light-emitting device of the present invention.

FIG. 3 is a schematic cross-sectional view illustrating a third embodiment of the organic light-emitting device of the present invention. The organic light-emitting device 30 shown in FIG. 3 is different from the organic light-emitting device 20 shown in FIG. 2 in that a light-emitting layer 3 is additionally provided between a hole-transporting layer 5 and an electron-transporting layer 6. The organic light-emitting device 30 has a configuration in which the functions of carrier transportation and light emission are separated from each other, so that organic compounds having characteristics of hole-transporting property, electron-transporting property and light-emitting property, respectively, can suitably be combined and used. Therefore, since the degree of freedom in selecting materials can significantly be increased, and further since various organic compounds having different emission wavelengths can be used, a wide variety of emission hues can be provided. Further, it also becomes possible to effectively confine carriers or excitons in the light-emitting layer 3 at the central portion, thereby improving the emission efficiency.

Figure 4:
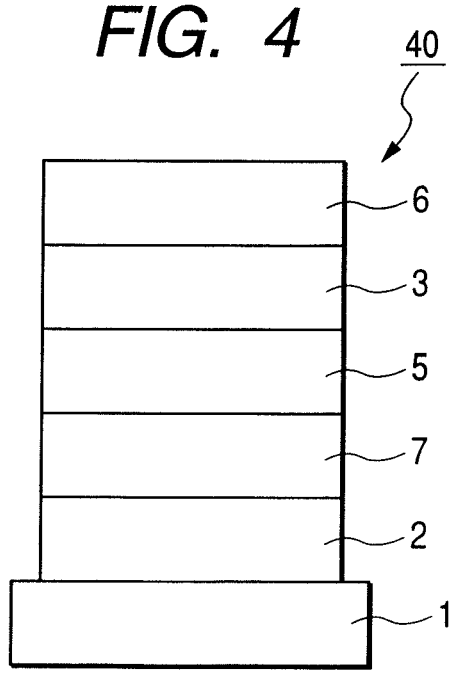
FIG. 4 is a cross-sectional view illustrating a fourth embodiment of the organic light-emitting device of the present invention.

FIG. 4 is a schematic cross-sectional view illustrating a fourth embodiment of the organic light-emitting device of the present invention. The organic light-emitting device 40 shown in FIG. 4 is different from the organic light-emitting device 30 shown in FIG. 3 in that a hole injection layer 7 is additionally provided between an anode 2 and a hole-transporting layer 5. In the organic light-emitting device 40, by additionally providing the hole injection layer 7, the adhesion between the anode 2 and the hole-transporting layer 5 or the hole injection property is improved, so that the driving voltage can be effectively reduced.

Figure 5:
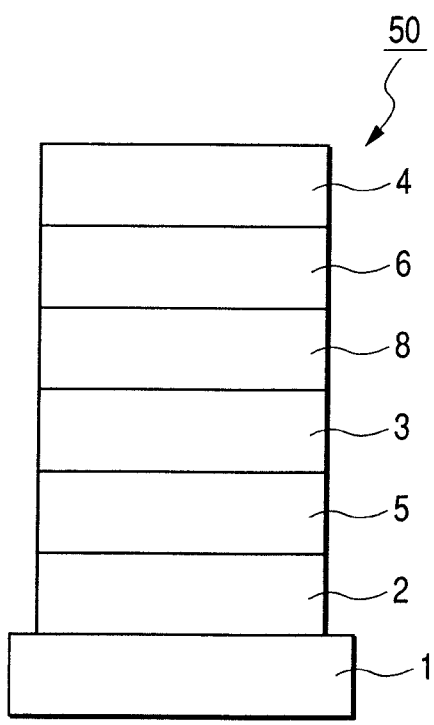
FIG. 5 is a cross-sectional view illustrating a fifth embodiment of the organic light-emitting device of the present invention.

FIG. 5 is a schematic cross-sectional view illustrating a fifth embodiment of the organic light-emitting device of the present invention. The organic light-emitting device 50 shown in FIG. 5 is different from the organic light-emitting device 30 shown in FIG. 3 in that a layer (hole/exciton blocking layer 8) for blocking holes or excitons from passing to a cathode 4 side is additionally provided between a light-emitting layer 3 and an electron-transporting layer 6. The configuration improves the emission efficiency of the organic light-emitting device 50 by using an organic compound with a significantly high ionization potential as the hole/exciton blocking layer 8.

Figure 6:
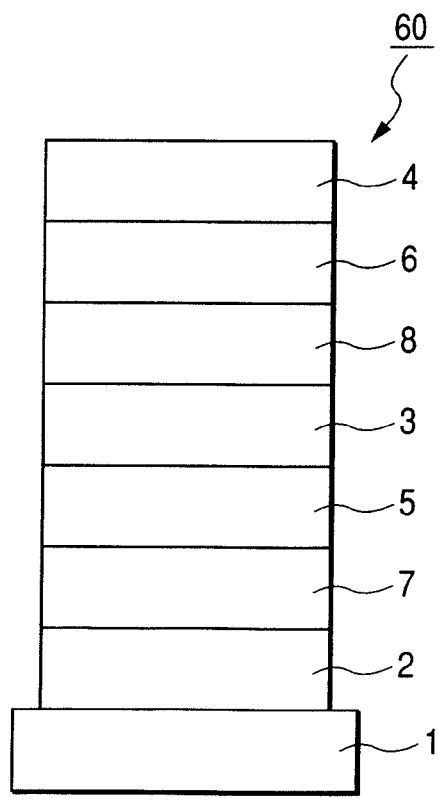
FIG. 6 is a cross-sectional view illustrating a sixth embodiment of the organic light-emitting device of the present invention.

FIG. 6 is a cross-sectional view illustrating a sixth embodiment of the organic light-emitting device of the present invention. The organic light-emitting device 60 shown in FIG. 6 is different from the organic light-emitting device 40 shown in FIG. 4 in that the hole/exciton-blocking layer 8 is additionally provided between the light-emitting layer 3 and the electron-transporting layer 6. By using an organic compound having an extremely high ionization potential as the hole/exciton blocking layer 8, the emission efficiency of the organic light-emitting device 60 can be improved.

FIGS. 1 to 6 merely show very basic device configurations and the configuration of the organic light-emitting device containing the naphthalene compound according to the present invention is not limited thereto. For example, it is possible to adopt various layer structures, such as one in which an insulating layer, an adhesive layer, or an interference layer is formed at an interface between an electrode and an organic layer. Further, a hole-transporting layer 5 is composed of two layers having different ionization potentials.

The fused ring aromatic compound of the present invention has excellent light-emitting property and durability as compared to the conventional compounds and can be used in any one of the embodiments shown in FIGS. 1 to 6. At that time, the fused ring aromatic compound of the present invention may be used alone, or a plurality of compounds may be used in combination.

The fused ring aromatic compound of the present invention is contained in any one of the above-mentioned layers formed of an organic compound, for example, the light-emitting layer 3, the hole-transporting layer 5, the electron-transporting layer 6, the hole injection layer 7, and the hole/exciton blocking layer 8 shown in FIGS. 1 to 6, preferably in either one of the light-emitting layer 3 and the electron-transporting layer 6, more preferably in the light-emitting layer 3. At that time, the fused ring aromatic compound of the present invention contained in the layer may either be of a single kind or of two or more kinds.

Further, the light-emitting layer 3 is preferably formed of a host and a guest, and the guest is preferably the fused ring aromatic compound of the present invention. Incidentally, the term "guest" as herein employed refers to a compound that emits light in response to recombination between holes and electrons in an emission region of the organic light-emitting device, and the guest is contained, together with a substance (host) forming the emission region, in the light-emitting layer 3.

When a light-emitting layer is formed of a carrier transporting host and a guest, the process for light emission is composed of the following several steps.

1. Transportation of electrons/holes in the light-emitting layer
2. Generation of excitons in the host
3. Transmission of excitation energy between host molecules
4. Transfer of the excitation energy from the host to the guest The desired energy transfer and light emission in the respective steps are caused in competition with various deactivation steps.

It is needless to say that in order to increase the emission efficiency of an organic light-emitting device, the emission quantum yield of a luminescent center material itself needs to be increased. However, how high efficiency of energy transfer between hosts or between a host and a guest can be achieved is also a large problem. In addition, the cause for degradation of light emission due to energization has not been clarified yet. However, it is assumed that the degradation is related at least to a luminescent center material itself or an environmental change of a light-emitting material due to surrounding molecules.

The use of the fused ring aromatic compound of the present invention particularly as a guest for a light-emitting layer can provide a device which has good emission efficiency, maintains high luminance for a long period of time, and is less susceptible to energization degradation When the fused ring aromatic compound of the present invention is used as a guest for a light-emitting layer, the content of the compound based on the weight of all materials which constitute the light-emitting layer is preferably 50 wt % or less, more preferably 0.1 wt % or more and 30 wt % or less, and particularly preferably 0.1 wt % or more and 15 wt % or less.

Further, when the fused ring aromatic compound of the present invention is used as a guest of a light-emitting layer, the host is not particularly limited, but is also preferably a fused ring aromatic compound from the viewpoint of compatibility between the host and the guest. Preferable examples of the fused ring aromatic compound as the host include anthracene derivatives, naphthalene derivatives, fluorene derivatives, pyrene derivatives, fluoranthene derivatives and perylene derivatives. Considering also the viewpoint of carrier-transporting property, fluorene derivatives and pyrene derivatives are more preferable as the host. A compound having a fluorene ring and a pyrene ring in a molecule is still more preferable as the host.

Hereinafter, preferable specific structural formulas of a host used for the organic light-emitting device of the present invention are shown below. However, these formulas represent only typical examples and the present invention should not be limited to thereto.
Pyrene Derivatives
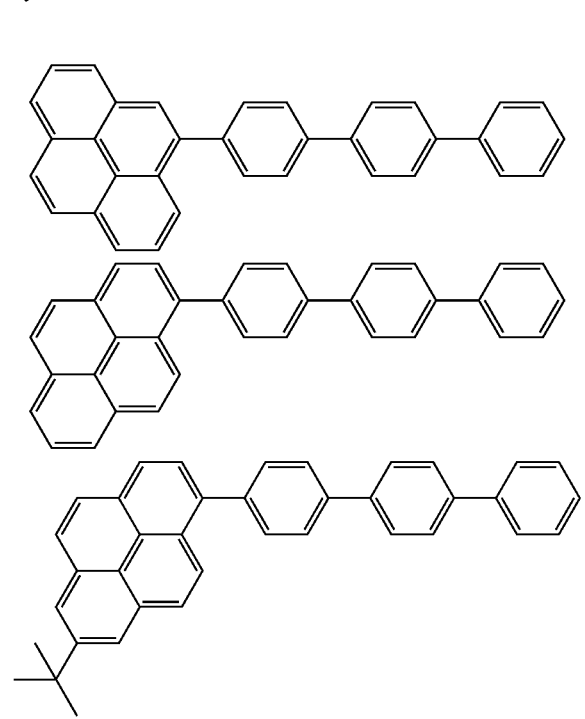
-continued
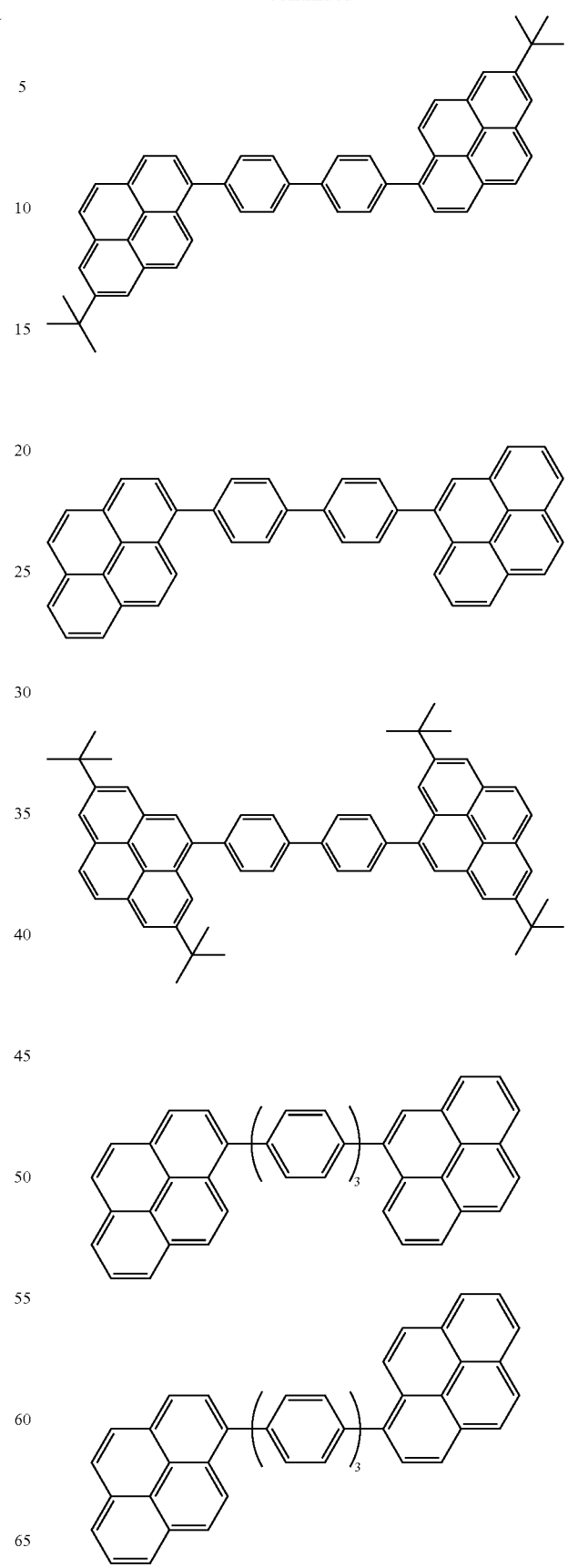

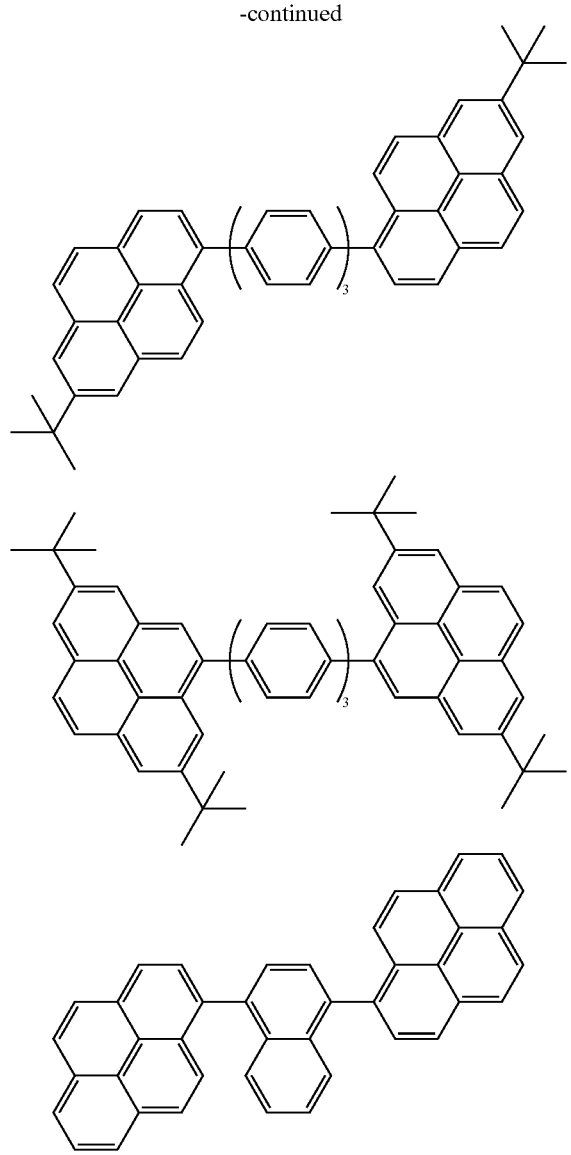
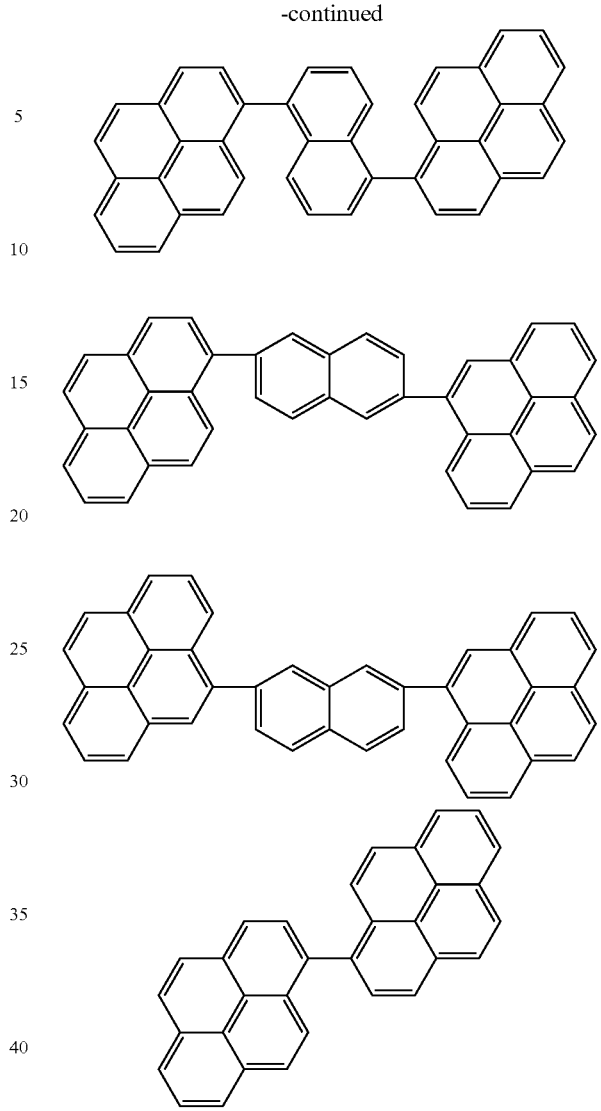
Fluorene Derivatives
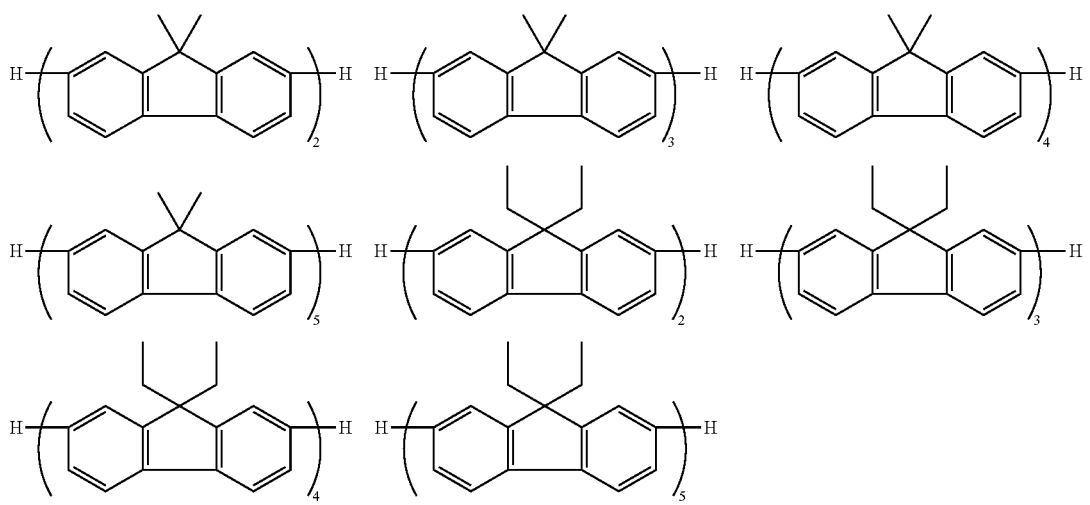

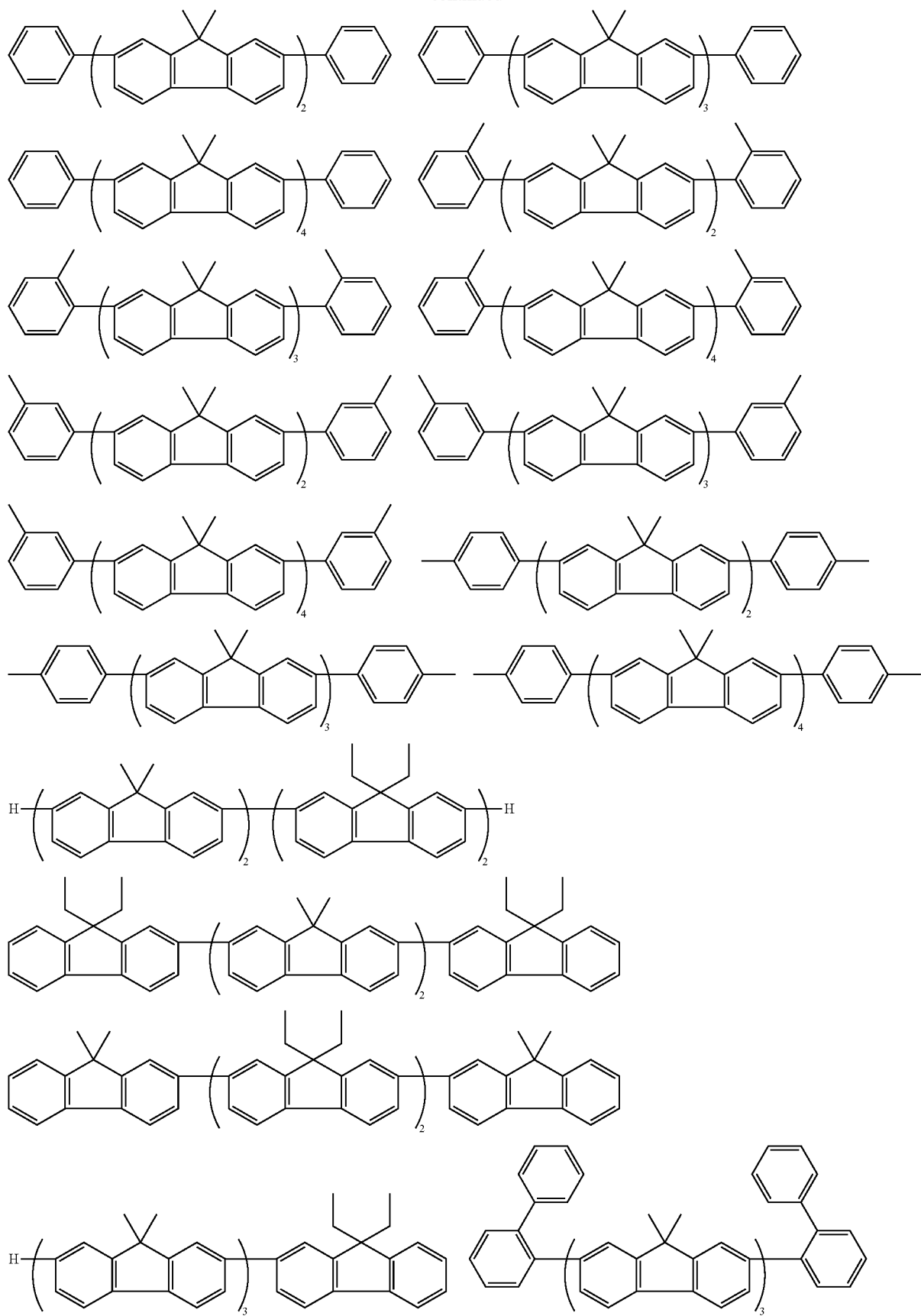

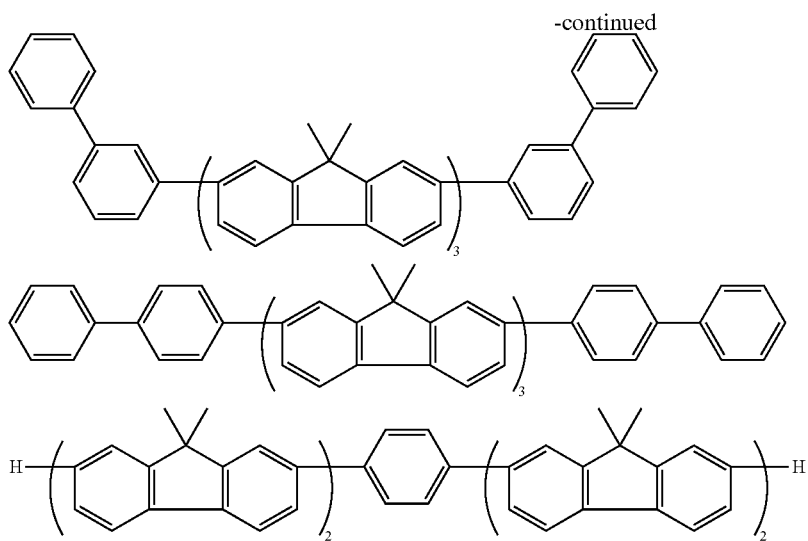
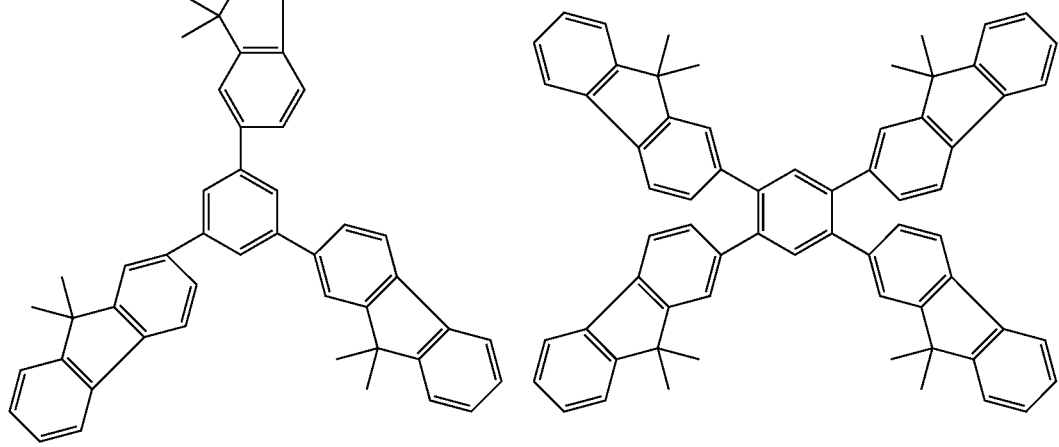
Compound Having Fluorene Ring and Pyrene Ring
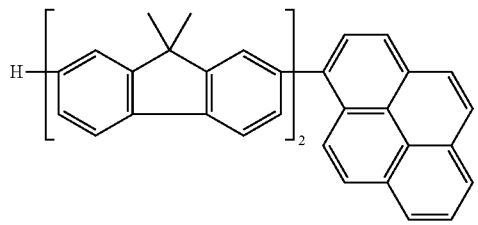
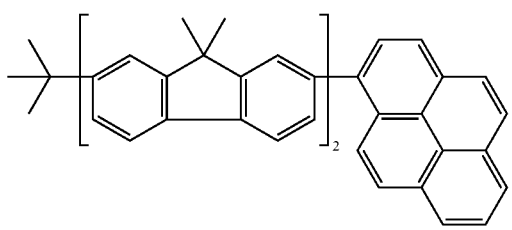
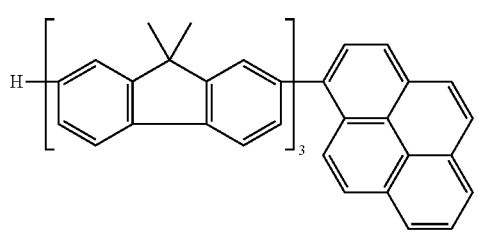
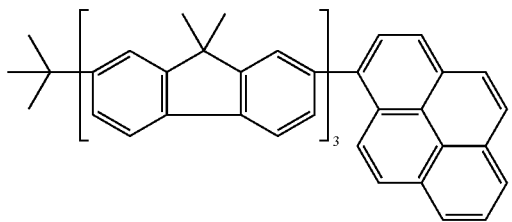

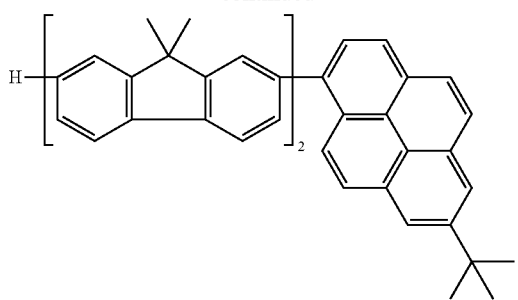
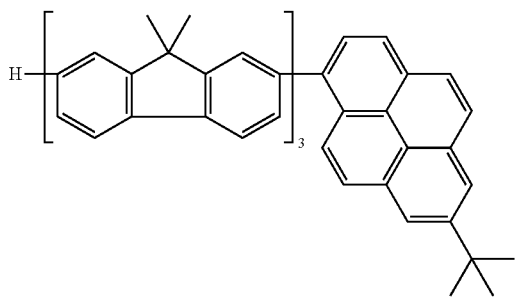
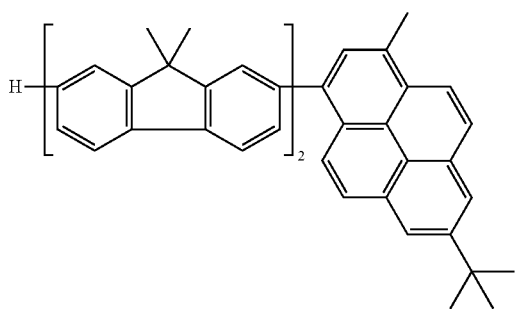
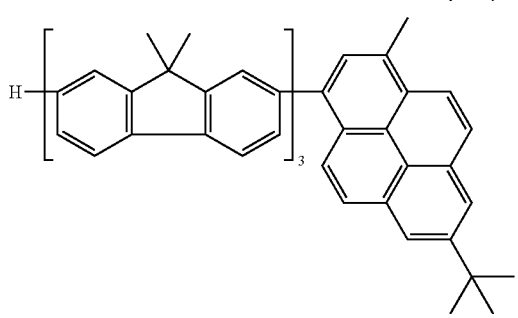
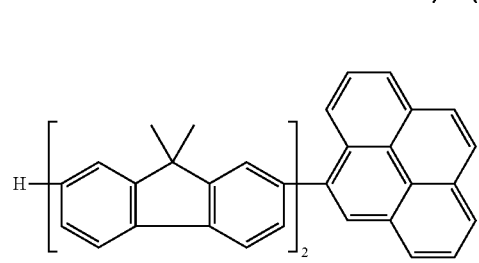
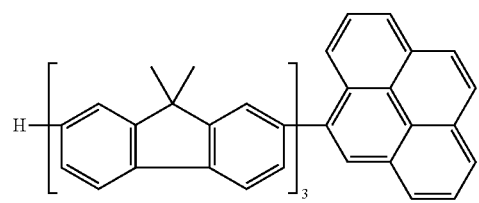
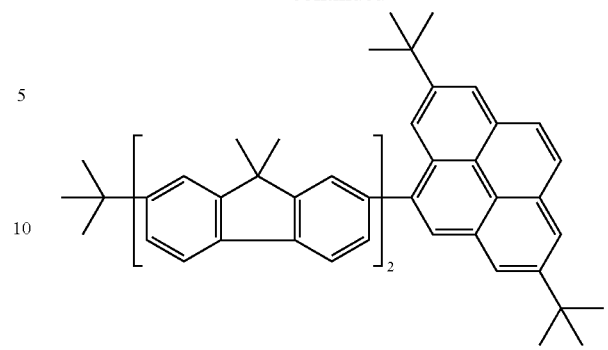
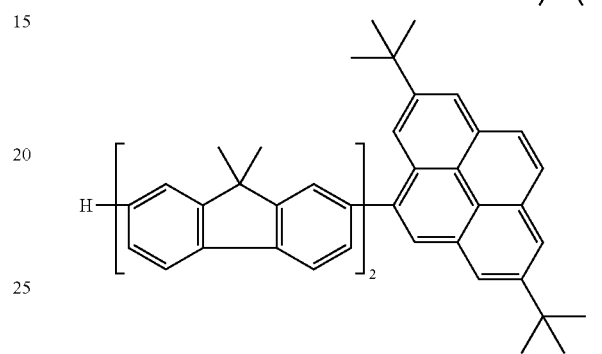
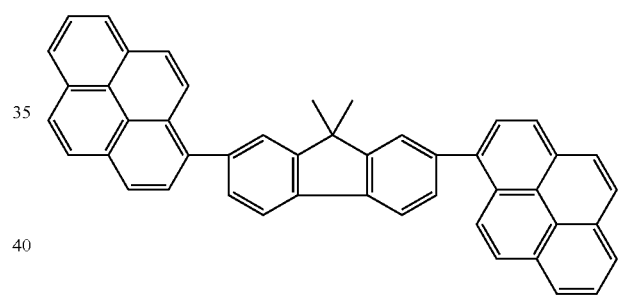
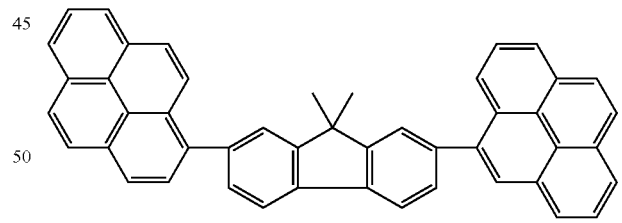
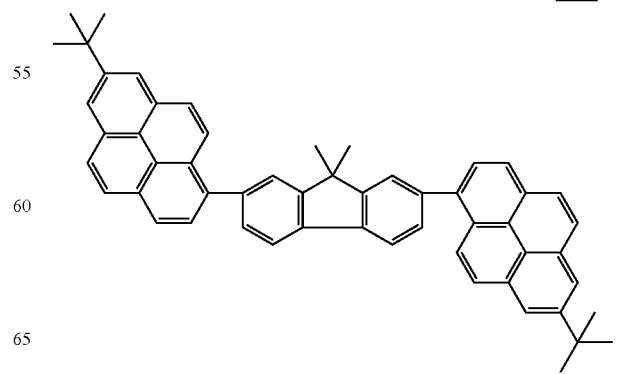

51
-continued
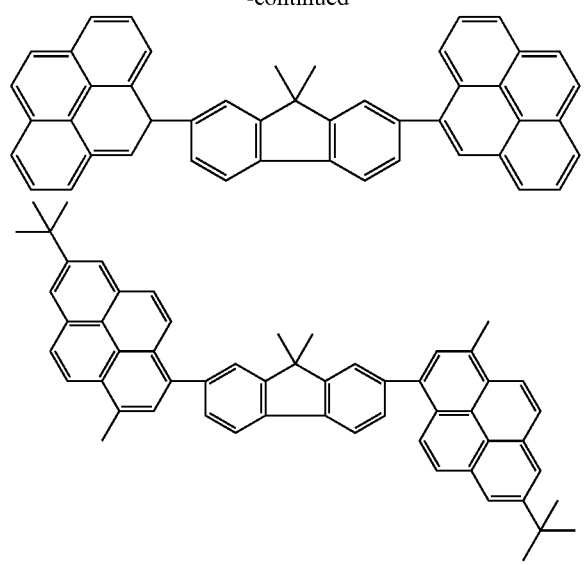
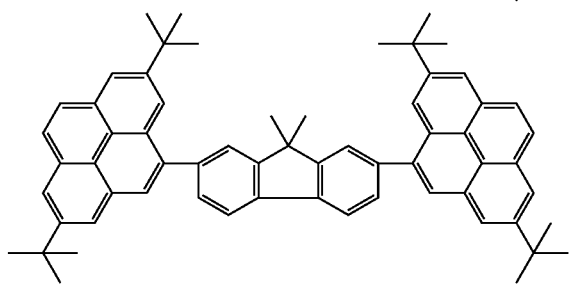
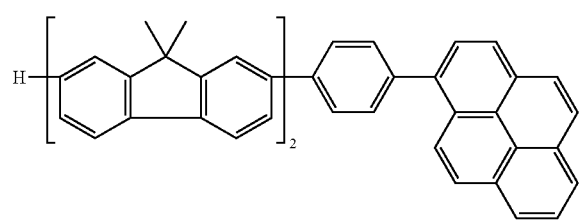
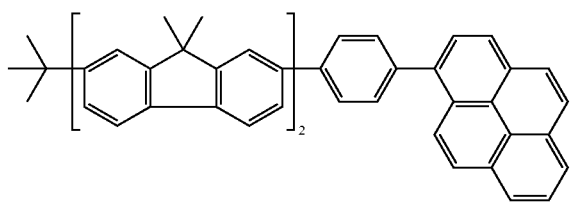
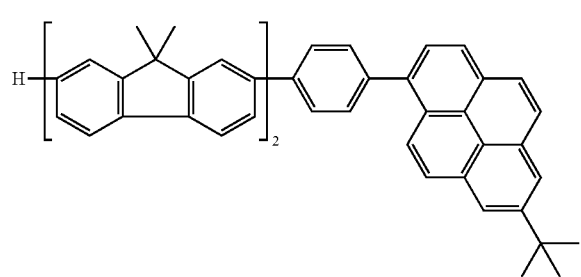
52
-continued
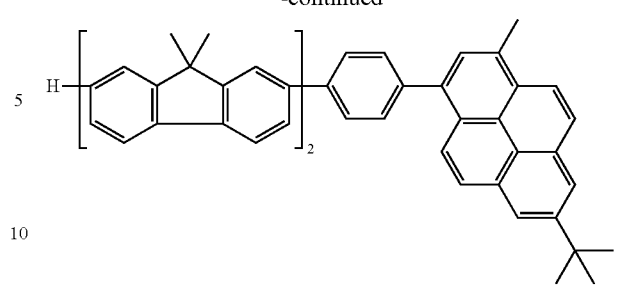
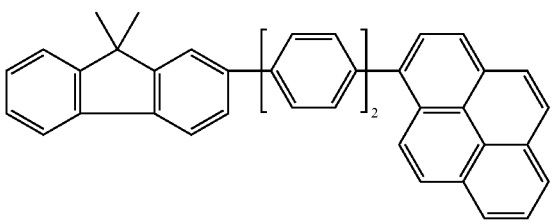
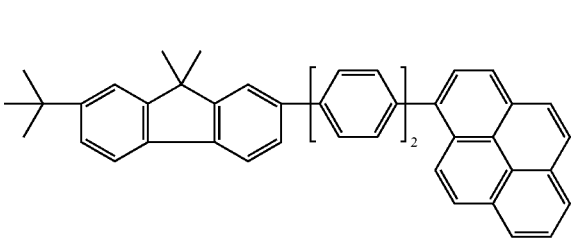
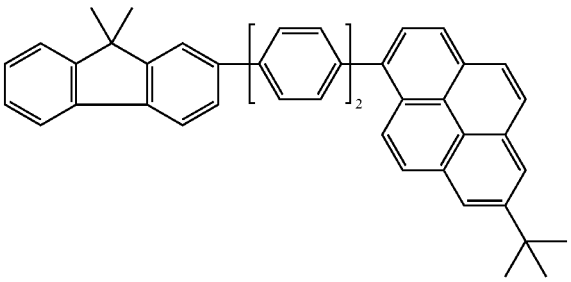

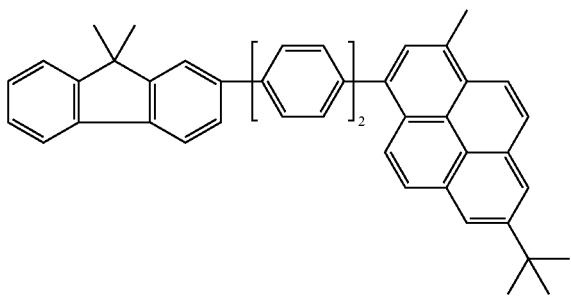

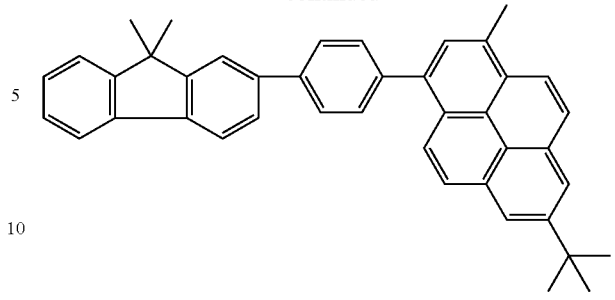

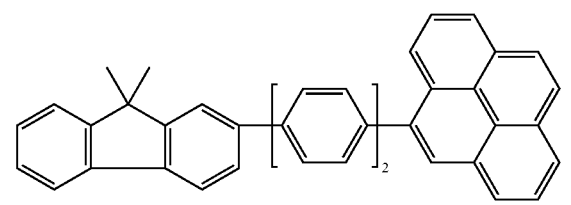

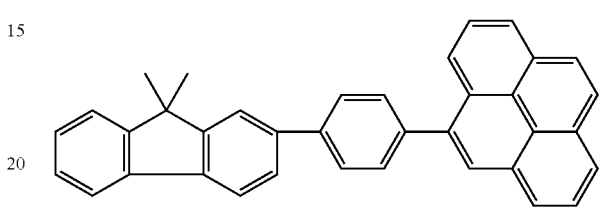

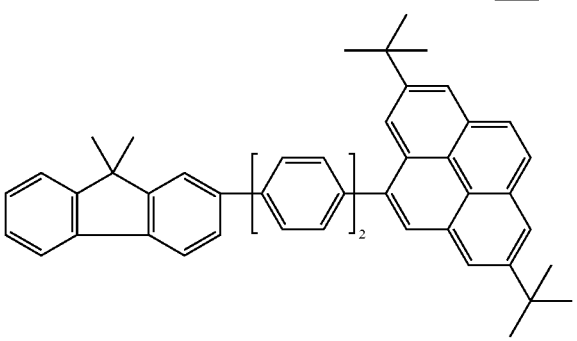

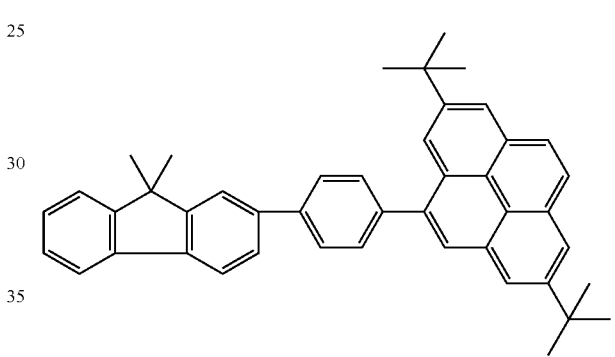

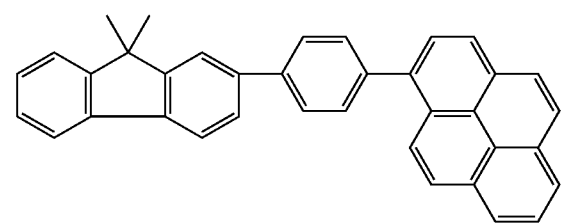

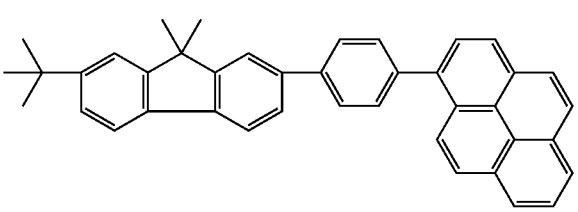

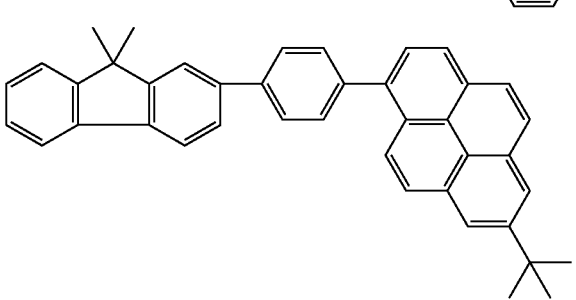

In the meantime, the fused ring aromatic compound of the present invention may be used as a host of a light-emitting layer. In this case, the guest is not particularly limited, and compounds described later can be appropriately used depending on a desired emission color or the like as the guest. Further, as needed, a hole-transporting compound, an electron-transporting compound or the like, in addition to the guest, can also be used together as a dopant and used. When the fused ring aromatic compound of the present invention is used as a host of a light-emitting layer, the content is preferably 50 wt % or more and 99.9 wt % or less based on the total weight of materials constituting the light-emitting layer.

The fused ring aromatic compound of the present invention may be contained only in a light-emitting layer as a layer formed of an organic compound, but it may be contained, for example, in a hole injection layer, a hole-transporting layer, an electron injection layer, an electron-transporting layer, or an electron-blocking layer, as needed, in addition to the light-emitting layer.

In the organic light-emitting device of the present invention, the fused ring aromatic compound of the present invention is preferably used as a component constituting either an electron-transporting layer or a light-emitting layer, but a known hole-transporting compound, light-emitting compound or electron-transporting compound can also be used together, as needed.

Examples of these compounds are shown below.

Hole-transporting Compounds
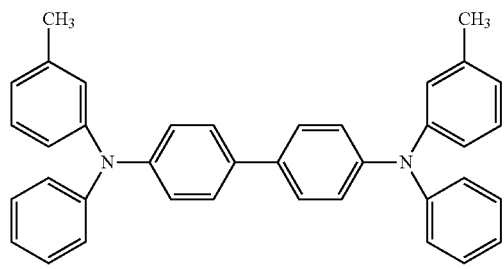
TPD
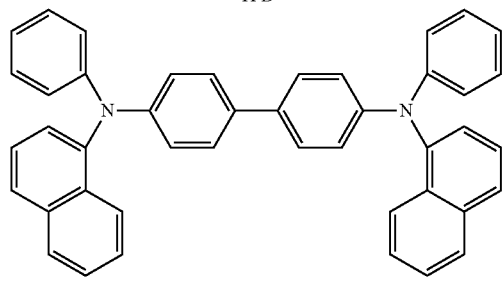
a-NPD
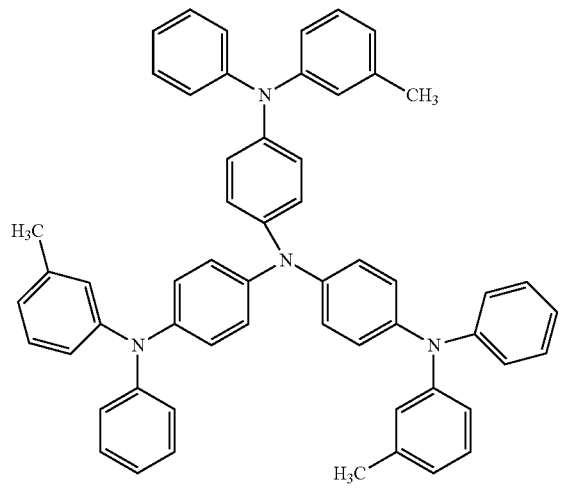
m-MTDATA
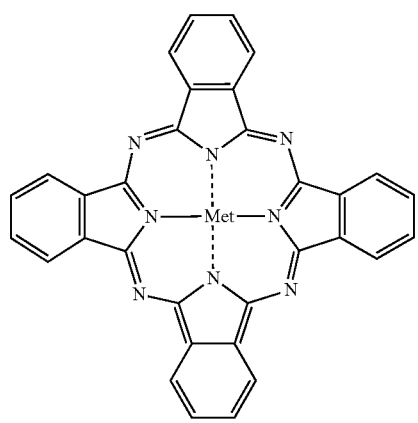
Met: Cu, Mg, AlCl, TiO, SnCl2 etc
Met-Pc
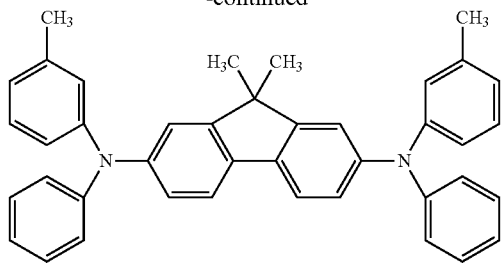
DTDPFL
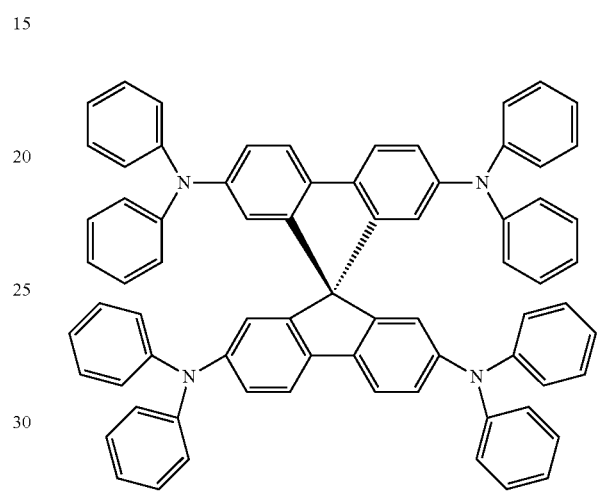
spiro-TPD
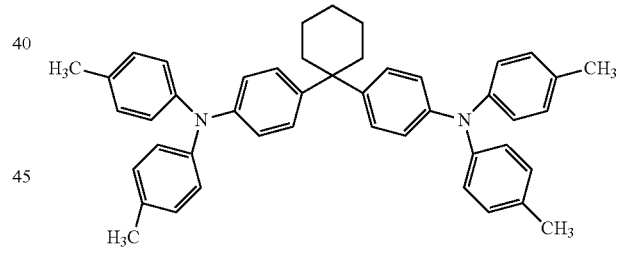
TPAC
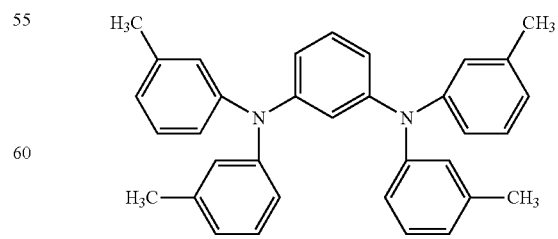
PDA Electron-transporting/Light-emitting Materials
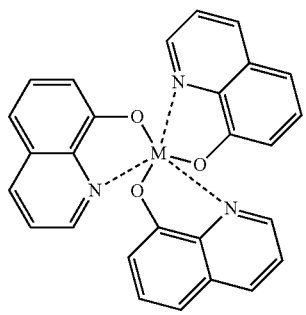
M: Al, Ga
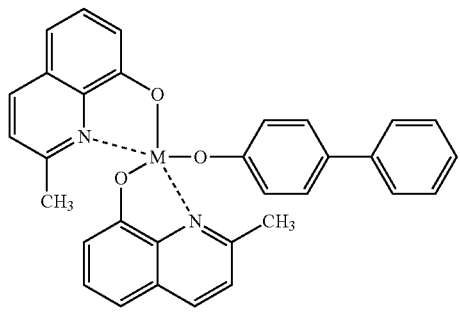
M: Al, Ga
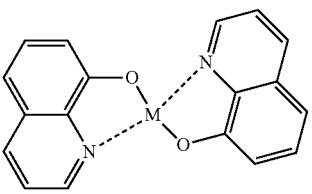
M: Zn, Mg, Be
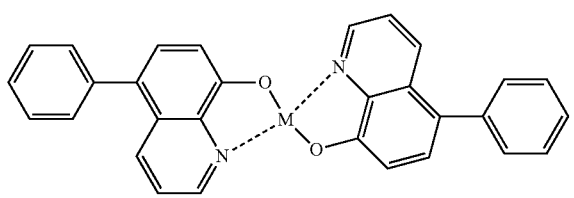
M: Zn, Mg, Be
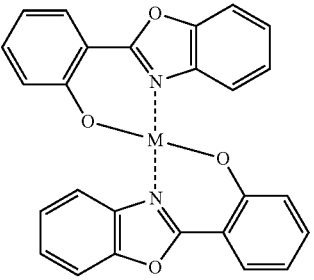
M: Zn, Mg, Be
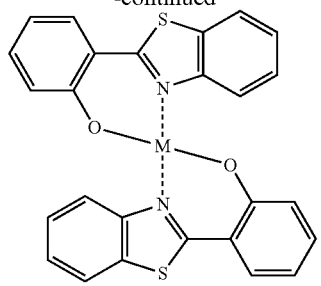
M: Zn, Mg, Be
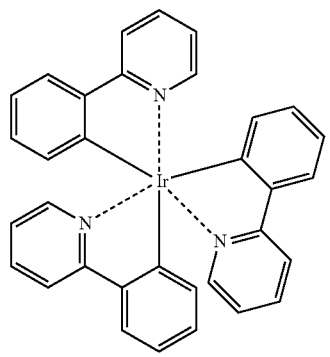
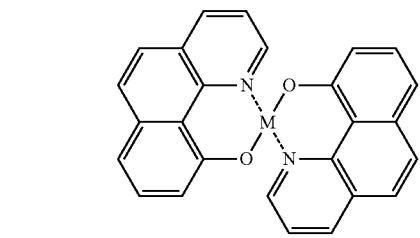
M: Zn, Mg, Be
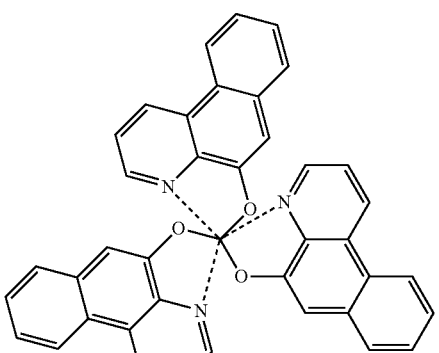
M: Al, Ga Light-emitting Materials
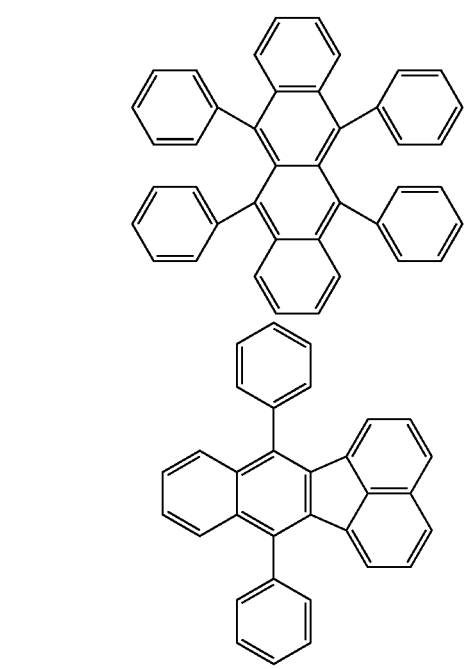
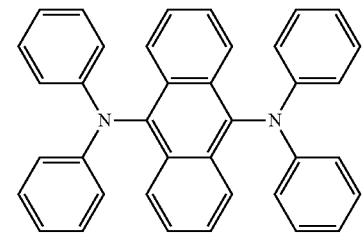
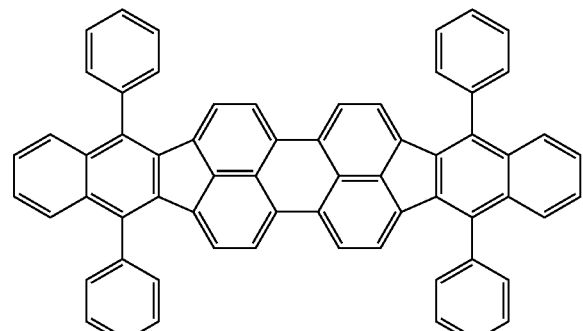
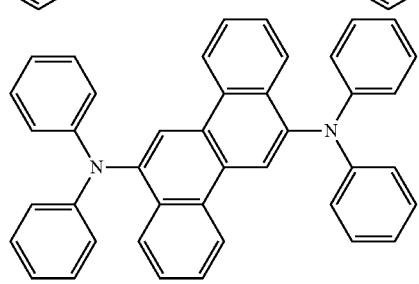
-continued
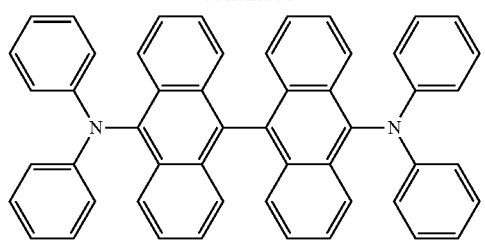
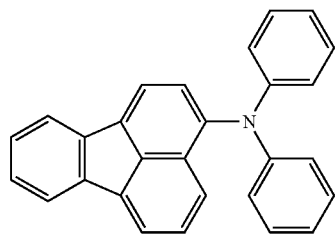
Light-emitting Layer Matrix Materials and Electron-transporting Materials
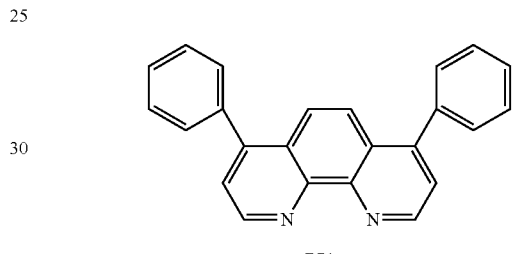
BPhen
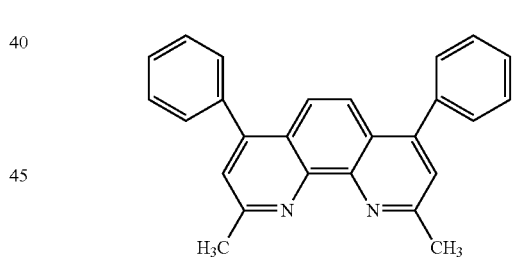
BCP
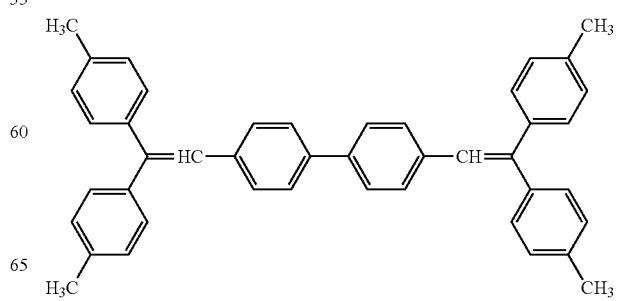

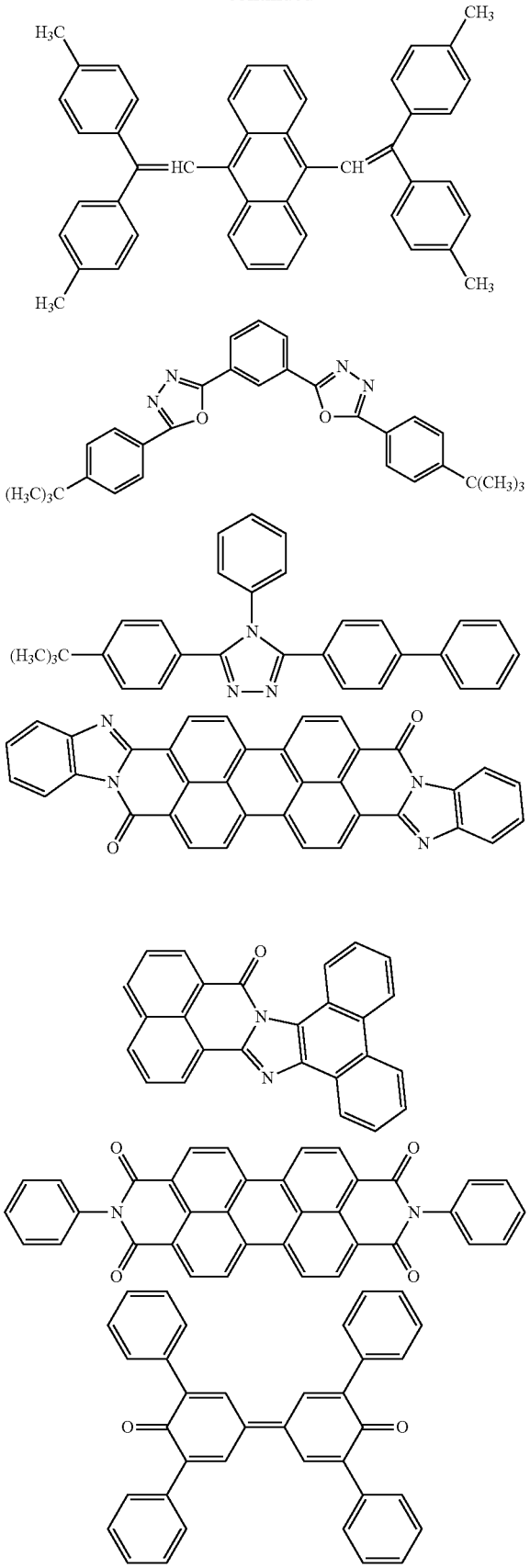

An anode material used for the organic light-emitting device of the present invention preferably has as large a work function as possible, and includes, for instance, an elemental metal such as gold, platinum, nickel, palladium, cobalt, selenium, and vanadium, an alloy thereof, and a metal oxide such as tin oxide, zinc oxide, indium tin oxide (ITO) and indium zinc oxide. Further, a conductive polymer such as polyaniline, polypyrrole, polythiophene and polyphenylene sulfide can be employed. These electrode materials can be used singly or in combination.

On the other hand, a cathode material used for the organic light-emitting device of the present invention preferably has a low work function, and include, for instance, an elemental metal such as lithium, sodium, potassium, cesium, calcium, magnesium, aluminum, indium, silver, lead, tin, and chromium. Alternatively, an alloy made of a plurality of the above metals can also be used. A metal oxide such as indium tin oxide (ITO) can be also utilized. In addition, the cathode may be either of a single layer configuration or of a multilayer configuration.

A substrate used for the organic light-emitting device of the present invention is not particularly limited, but an opaque substrate such as a metal substrate and a ceramic substrate or a transparent substrate such as glass, quartz, and a plastic sheet is used. Further, it is also possible to employ, for a substrate, a color filter film, a fluorescent color conversion filter film and a dielectric reflection film to thereby control the emission color.

Incidentally, after the organic light-emitting device has been produced, a protective layer or an encapsulation layer may further be provided, for the purpose of preventing contact with oxygen or moisture. Examples of such a protective layer include a diamond thin film; a film of an inorganic material such as a metal oxide and a metal nitride; a film of a polymer such as a fluororesin, poly-p-xylene, polyethylene, silicone resin, and polystyrene resin; and further a photocurable resin. Further, the produced device may also be covered with glass, a gas-impermeable film and a metal, or be packaged with a suitable encapsulation resin.

In the organic light-emitting device of the present invention, a layer containing the fused ring aromatic compound of the present invention and other layers containing an inorganic compound are formed by the below-mentioned methods. Generally, a thin film is formed by a vacuum evaporation method or a coating method of applying an organic compound dissolved in a suitable solvent. Particularly, when the film is formed by the coating method, the film can be formed by additionally using a suitable binder resin.

The above described binder resin can be selected from a wide range of binding resins, and includes, for instance, polyvinylcarbazole resin, polycarbonate resin, polyester resin, polyarylate resin, polystyrene resin, acrylic resin, methacrylic resin, butyral resin, polyvinylacetal resin, diallylphthalate resin, phenolic resin, epoxy resin, silicone resin, polysulfonic resin and urea resin, but is not limited to them.

In the organic light-emitting device of the present invention, a layer including the fused ring aromatic compound of the present invention is made to have a film thickness of 10 μm or less, preferably 0.5 μm or less, and more preferably 0.01 μm or more and 0.5 μm or less.

EXAMPLES

The present invention will be more specifically described below by means of examples, but should not be limited to these examples.

Example 1

Synthesis of Exemplified Compound No. A-2

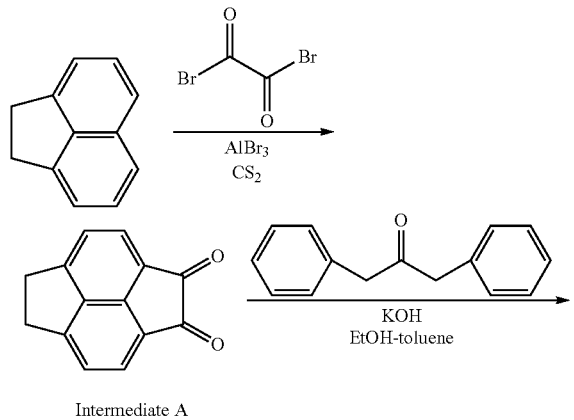

Intermediate A

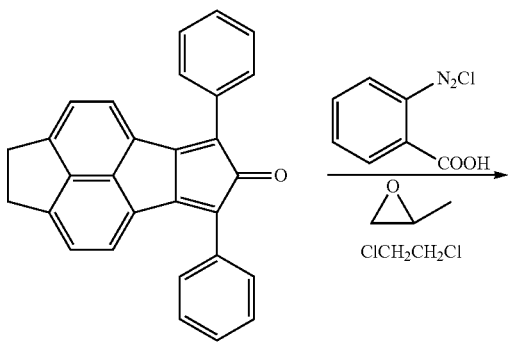

Intermediate B

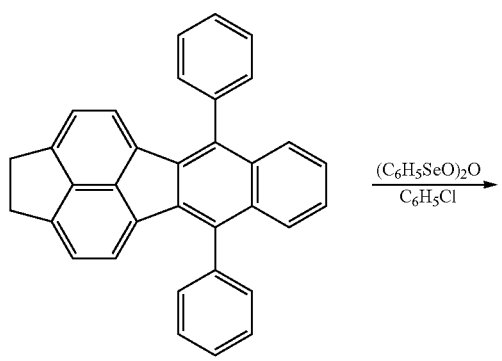

Intermediate C

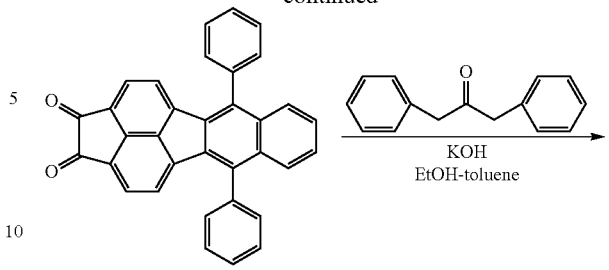

Intermediate D

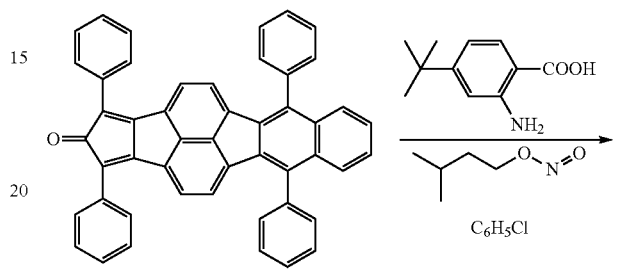

Intermediate E

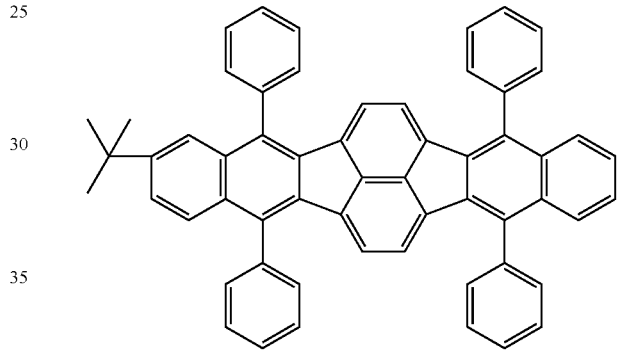

A-2

Synthesis of Intermediate A

Acenaphthene (52.8 g, 0.34 mol) and 4.5 L of carbon disulfide were placed in an argon-purged reaction vessel, and the reaction solution was then cooled to 0° C. in an ice bath. After oxalyl bromide (75.0 g, 0.35 mol) was added to this reaction solution, aluminum bromide (anhydrous) (187.5 g, 0.70 mol) was slowly added thereto and the reaction solution was stirred for 1 hour. After the temperature of the reaction solution was returned to room temperature, and then carbon disulfide was removed by decantation. 3 L of a 10% HCl solution was added to the reaction solution under an ice bath and the solution was stirred for 2 hours, and then filtered. The obtained crystal was washed sequentially with methanol and isopropyl ether to obtain a brown solid. This brown solid was dissolved in chloroform and purified by silica gel chromatography (developing solvent: chloroform), and then recrystallized with chloroform to thereby obtain 16.4 g of an intermediate A (78.8 mmol, yield 23%).

Synthesis of Intermediate B

The intermediate A (10.0 g, 48 mmol), 150 mL of ethanol, 15 mL of toluene were charged into a reaction vessel, and 1,3-diphenyl-2-propanon (10.0 g, 48 mmol) was added to the solution and then 20 ml of a 6N KOH aqueous solution was slowly added dropwise thereto. Next, the reaction solution was heated and stirred for 15 minutes in an oil bath at 80° C. The temperature of the reaction solution was returned to room temperature and a small amount of water was added thereto and the reaction solution was then filtered. The obtained crystal was washed sequentially with water, methanol and isopropyl ether, and then dried under reduced pressure to thereby obtain 15.8 g of an intermediate B (41.4 mmol, yield 86%).

Synthesis of Intermediate C

The following reagents and solvents were charged into a reaction vessel.
Intermediate B: 8.0 g (21 mmol)
1,2-Dichloroethane: 160 mL
Benzenediazonium-2-carboxylate hydride: 4.0 g (23 mmol)
Propylene oxide: 5.0 g (83 mmol)
Next, the reaction solution was heated and stirred in an oil bath at 80° C. for 1 hour. After the temperature of the reaction solution was returned to room temperature, the solvent was evaporated under reduced pressure to obtain a brown solid. This brown solid was purified by silica gel chromatography (developing solvent: chloroform/hexane=1/2), and then recrystallized from chloroform/ethanol to thereby obtain 7.0 g of an intermediate C (16.3 mmol, yield 77%).

Synthesis of Intermediate D

The intermediate C (5.0 g, 12 mmol), 260 mL of chlorobenzene, benzeneseleninic anhydride (purity 70%) (produced by Aldrich) (8.5 g, 23 mmol) were charged into a reaction vessel, and the reaction solution was heated and stirred for 12 hours in an oil bath at 135° C. After the temperature of the reaction solution was returned to room temperature, the solvent was evaporated under reduced pressure to obtain a reddish brown solid. This reddish brown solid was purified by silica gel chromatography (developing solvent: chloroform/hexane=1/5) to thereby obtain 4.9 g of an intermediate D (10.7 mmol, yield 92%).

Synthesis of Intermediate E

The intermediate D (4.0 g, 8.7 mmol), 50 mL of ethanol, 5 mL of toluene were charged into a reaction vessel, and 1,3-diphenyl-2-propanone (1.8 g, 8.7 mmol) was added to the solution and then 4 mL of a 6N-KOH aqueous solution was slowly added dropwise thereto. Next, the reaction solution was heated and stirred for 30 minutes in an oil bath at 80° C. Thereafter, the temperature of the reaction solution was returned to room temperature and a small amount of water was added thereto and the reaction solution was then filtered. The obtained crystal was washed sequentially with water, methanol and isopropyl ether, and then dried under reduced pressure to thereby obtain 4.0 g of an intermediate E (6.3 mmol, yield 73%).

Synthesis of Exemplified Compound A-2

The following reagents and solvents were charged into a reaction vessel.
Intermediate E: 630 mg (1.0 mmol)
Chlorobenzene: 20 mL
2-Amino-4-tertiary-butylbenzoic acid: 290 mg (1.5 mmol)
Next, after 0.2 mL of isoamyl nitrite was slowly added dropwise to the solution, the reaction solution was heated and stirred in an oil bath at 150° C. for 1 hour. Subsequently, after the temperature of the reaction solution was returned to room temperature, the solvent was evaporated under reduced pressure and the residue was purified by silica gel column chromatography (developing solvent: chloroform) to thereby obtain a yellow crystal. The obtained crystal was dried under vacuum and then subjected to sublimation purification to thereby obtain 516 mg of Exemplified Compound No. A-2 (0.7 mmol, yield 70%).

Then, 736.3 as M+ of this compound was confirmed by MALDI-TOF MS (Matrix Assisted Laser Desorption/Ionization-Time of Flight Mass Spectroscopy).

Further, the structure of this compound was confirmed by NMR measurement.

$^1$H-NMR (CDCl$_3$, 500 MHz) σ(ppm): 7.62-7.52 (m, 12H), 7.51-7.44 (m, 12H), 7.31 (m, 1H), 7.28 (m, 2H), 6.24 (d, 4H), 1.23 (s, 9H)

Example 2

Synthesis of Exemplified Compound No. A-11

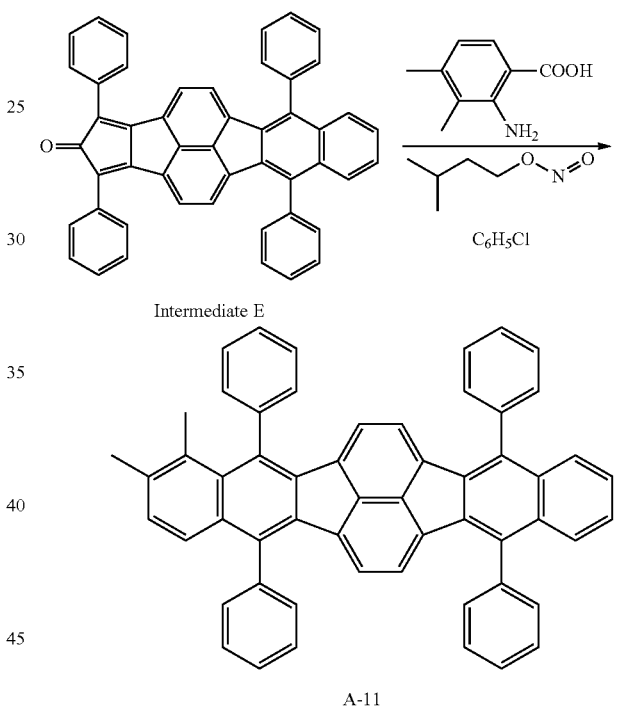

Intermediate E

A-11

The following reagents and solvents were charged into a reaction vessel.
Intermediate E: 630 mg (1.0 mmol)
Chlorobenzene: 20 mL
2-Amino-3,4-dimethylbenzoic acid: 248 mg (1.5 mmol)
Next, after 0.2 mL of isoamyl nitrite was slowly added dropwise to the solution, the reaction solution was heated and stirred in an oil bath at 150° C. for 1 hour. After the temperature of the reaction solution was returned to room temperature, the solvent was evaporated under reduced pressure and the residue was purified by silica gel column chromatography (developing solvent: chloroform) to thereby obtain a yellowish orange crystal. The obtained crystal was dried under vacuum and then subjected to sublimation purification to thereby obtain 480 mg of Exemplified Compound No. A-11 (0.7 mmol, yield 68%).

Then, 708.3 as M+ of this compound was confirmed by MALDI-TOF MS (Matrix Assisted Laser Desorption/Ionization-Time of Flight Mass Spectroscopy).

Further, the structure of this compound was confirmed by NMR measurement.

¹H-NMR (CDCl₃, 500 MHz) σ(ppm): 7.62-7.42 (m, 22H), 7.29 (m, 3H), 6.20 (d, 1H), 6.18 (d, 1H), 6.09 (d, 1H), 5.78 (d, 1H), 2.32 (s, 3H), 1.94 (s, 3H)

Example 3

Synthesis of Exemplified Compound No. B-20

Synthesis of Intermediate F

The following reagents and solvents were charged into a reaction vessel.

Intermediate D: 4.0 g (8.7 mmol)
Ethanol: 50 mL
Toluene: 5 mL

Next, after 1,3-bis(3,5-ditertiarybutylphenyl)-2-propanone (3.8 g, 8.7 mmol) was added to the solution, 4 ml of a 6N-KOH aqueous solution was slowly added dropwise

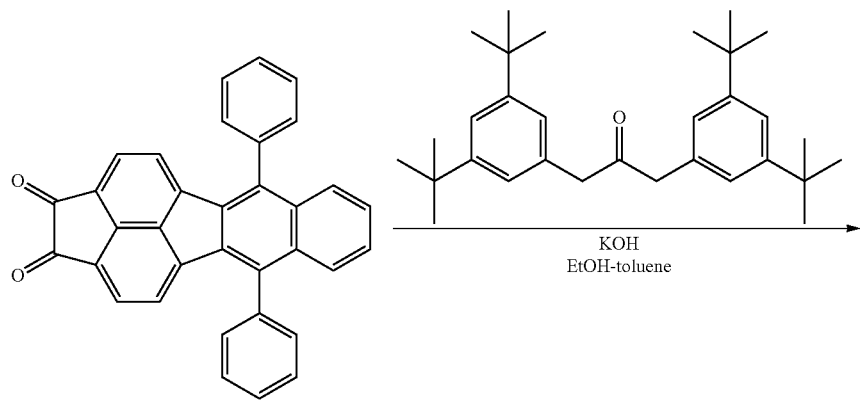

Intermediate D

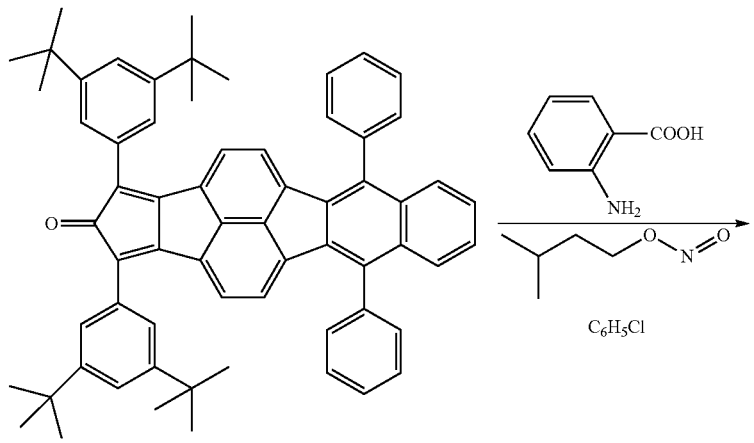

Intermediate F

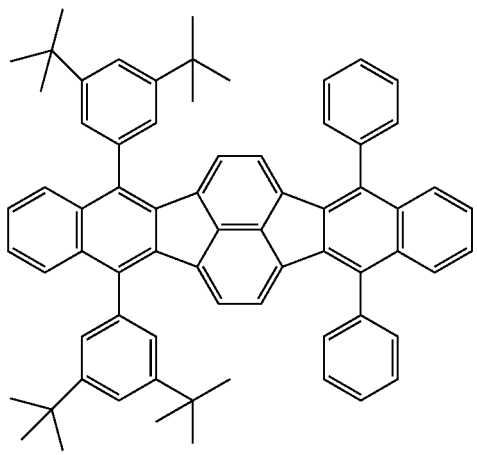

B-20 thereto. Subsequently, the reaction solution was heated and stirred for 30 minutes in an oil bath at 80° C. Thereafter, the temperature of the reaction solution was returned to room temperature and a small amount of water was added thereto and the reaction solution was then filtered. The obtained crystal was washed sequentially with water, methanol and isopropyl ether, and then dried under reduced pressure to thereby obtain 5.2 g of an intermediate F (6.1 mmol, yield 70%).

Synthesis of Exemplified Compound No. B-20

The following reagents and solvents were charged into a reaction vessel.
Intermediate F: 857 mg (1.0 mmol)
Chlorobenzene: 20 mL
2-Aminobenzoic acid: 205 mg (1.5 mmol)

Next, after 0.2 mL of isoamyl nitrite was slowly added dropwise to the solution, the reaction solution was heated and stirred in an oil bath at 150° C. for 1 hour. After the temperature of the reaction solution was returned to room temperature, the solvent was evaporated under reduced pressure and the residue was purified by silica gel column chromatography (developing solvent: chloroform) to thereby obtain a yellow crystal. The obtained crystal was dried under vacuum and then subjected to sublimation purification to thereby obtain 680 mg of Exemplified Compound No. B-20 (0.75 mmol, yield 75%).

Then, 904.5 as M+ of this compound was confirmed by MALDI-TOF MS (Matrix Assisted Laser Desorption/Ionization-Time of Flight Mass Spectroscopy).

Further, the structure of this compound was confirmed by NMR measurement.

$^1$H-NMR (CDCl$_3$, 500 MHz) σ(ppm): 7.62-7.57 (m, 10H), 7.51 (m, 6H), 7.35 (d, 4H), 7.34-7.27 (m, 4H), 6.27 (d, 4H), 6.20 (d, 4H), 1.53 (s, 36H)

Example 4

Synthesis of Exemplified Compound No. B-1

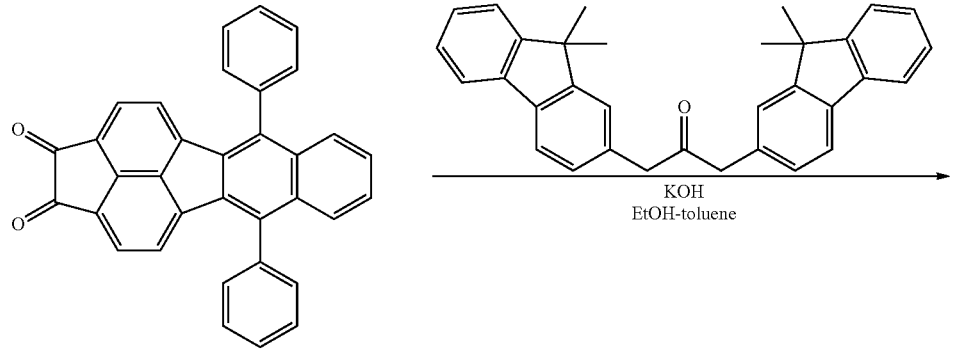

Intermediate D

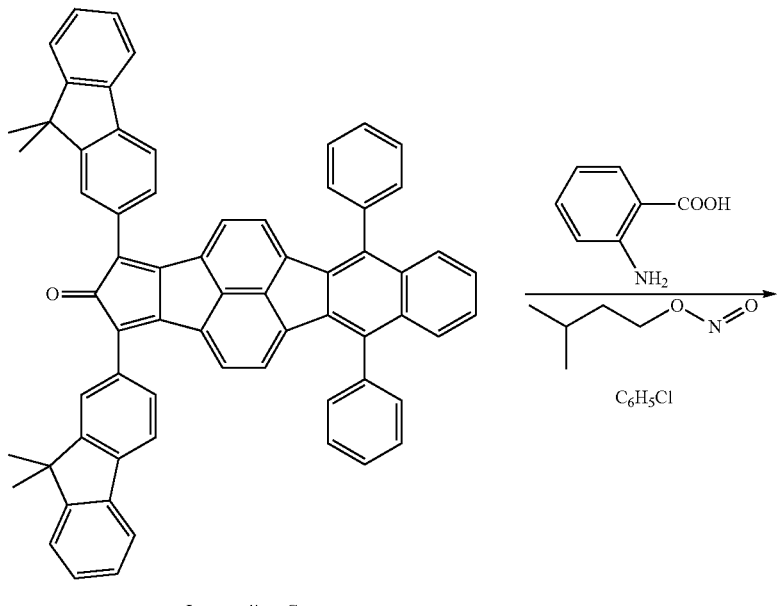

Intermediate G

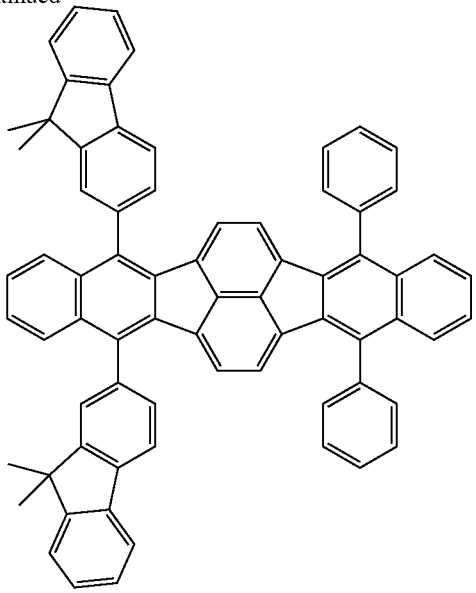

B-1

Synthesis of Intermediate G

The following reagents and solvents were charged into a reaction vessel.
Intermediate D: 4.0 g (8.7 mmol)
Ethanol: 50 mL
Toluene: 5 mL Next, after 1,3-bis[2(-9,9-dimethylfluorenyl)]-2-propanone (3.9 g, 8.7 mmol) was added to the solution, 4 ml of a 6N-KOH aqueous solution was slowly added dropwise thereto. Subsequently, the reaction solution was heated and stirred for 30 minutes in an oil bath at 80° C. Thereafter, the temperature of the reaction solution was returned to room temperature and a small amount of water was added thereto and the reaction solution was then filtered. The obtained crystal was washed sequentially with water, methanol and isopropyl ether, and then dried under reduced pressure to thereby obtain 5.3 g of an intermediate F (6.1 mmol, yield 70%).

Synthesis of Exemplified Compound No. B-1

The following reagents and solvents were charged into a reaction vessel.
Intermediate G: 865 mg (1.0 mmol)
Chlorobenzene: 20 mL
2-Aminobenzoic acid: 205 mg (1.5 mmol)

Next, after 0.2 mL of isoamyl nitrite was slowly added dropwise to the solution, the reaction solution was heated and stirred in an oil bath at 150° C. for 1 hour. After the temperature of the reaction solution was returned to room temperature, the solvent was evaporated under reduced pressure and the residue was purified by silica gel column chromatography (developing solvent: chloroform) to thereby obtain a yellow crystal. The obtained crystal was dried under vacuum and then subjected to sublimation purification to thereby obtain 600 mg of Exemplified Compound No. B-1 (0.66 mmol, yield 66%).

Then, 912.4 as M+ of this compound was confirmed by MALDI-TOF MS (Matrix Assisted Laser Desorption/Ionization-Time of Flight Mass Spectroscopy).

Further, the structure of this compound was confirmed by NMR measurement.

$^1$H-NMR (CDCl$_3$, 500 MHz) σ(ppm): 7.96 (d, 2H), 7.88 (d, 2H), 7.65 (m, 2H), 7.60-7.40 (m, 22H), 7.34 (m, 2H), 7.29 (m, 2H), 6.32 (d, 2H), 6.16 (d, 2H), 1.56 (s, 6H), 1.52 (s, 6H)

Example 5

Synthesis of Exemplified Compound No. C-11

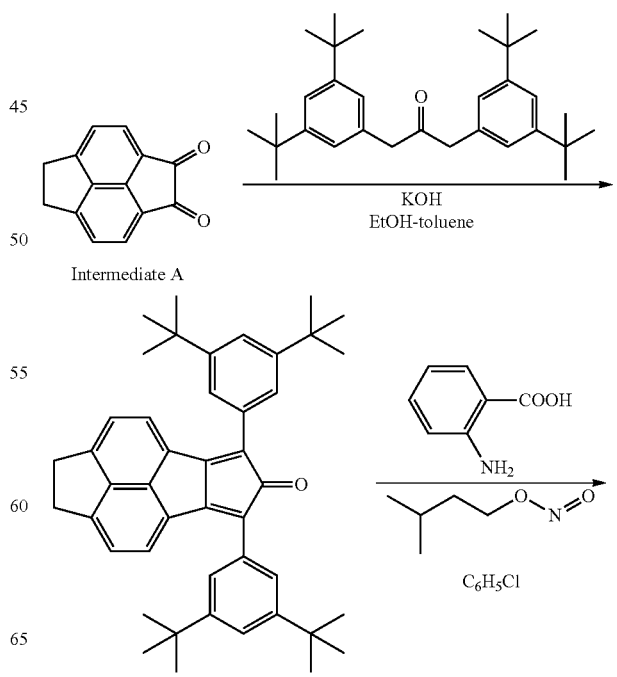

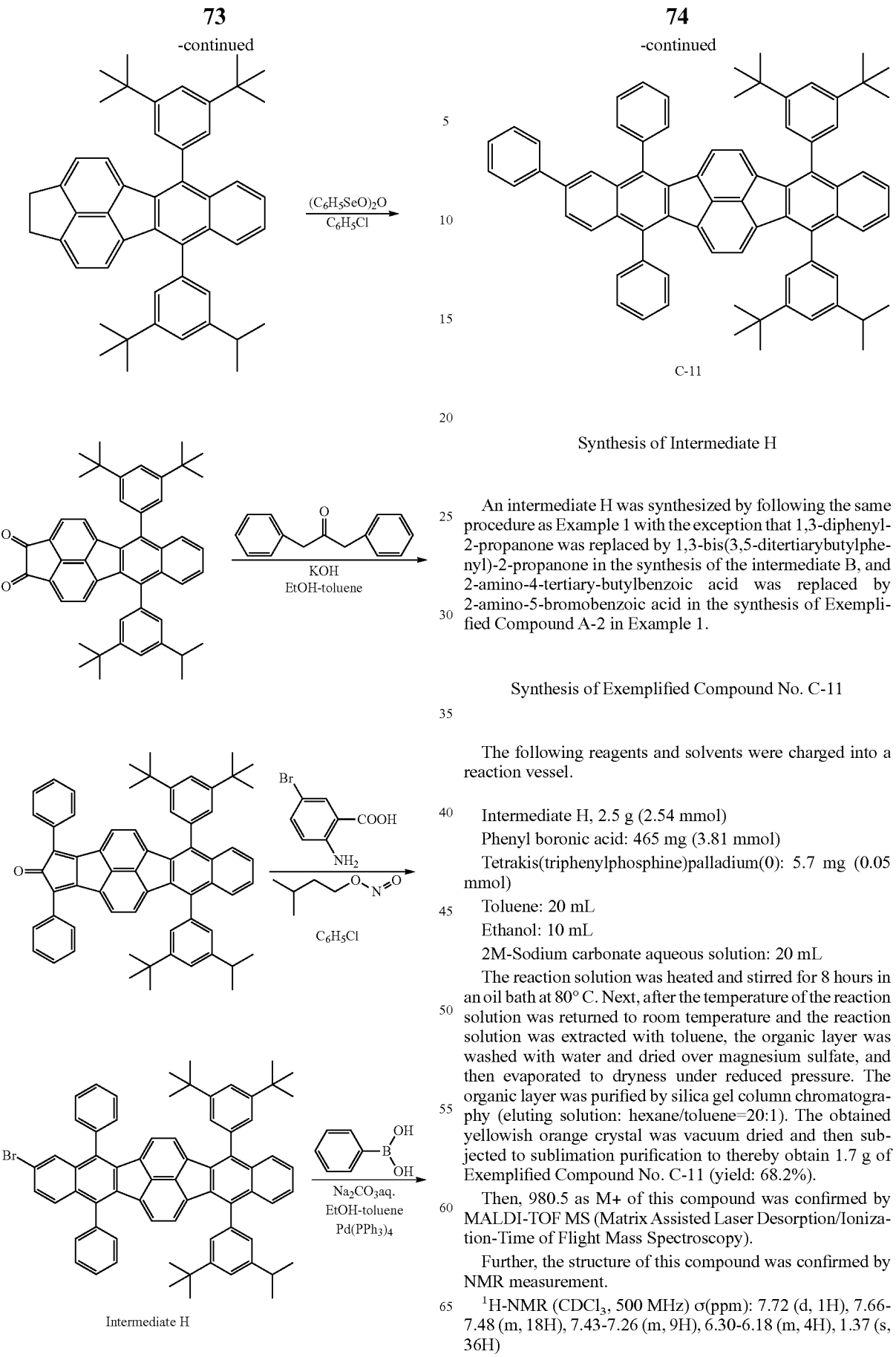

Synthesis of Intermediate H

An intermediate H was synthesized by following the same procedure as Example 1 with the exception that 1,3-diphenyl-2-propanone was replaced by 1,3-bis(3,5-ditertiarybutylphenyl)-2-propanone in the synthesis of the intermediate B, and 2-amino-4-tertiary-butylbenzoic acid was replaced by 2-amino-5-bromobenzoic acid in the synthesis of Exemplified Compound A-2 in Example 1.

Synthesis of Exemplified Compound No. C-11

The following reagents and solvents were charged into a reaction vessel.

Intermediate H, 2.5 g (2.54 mmol)
Phenyl boronic acid: 465 mg (3.81 mmol)
Tetrakis(triphenylphosphine)palladium(0): 5.7 mg (0.05 mmol)
Toluene: 20 mL
Ethanol: 10 mL
2M-Sodium carbonate aqueous solution: 20 mL The reaction solution was heated and stirred for 8 hours in an oil bath at 80° C. Next, after the temperature of the reaction solution was returned to room temperature and the reaction solution was extracted with toluene, the organic layer was washed with water and dried over magnesium sulfate, and then evaporated to dryness under reduced pressure. The organic layer was purified by silica gel column chromatography (eluting solution: hexane/toluene=20:1). The obtained yellowish orange crystal was vacuum dried and then subjected to sublimation purification to thereby obtain 1.7 g of Exemplified Compound No. C-11 (yield: 68.2%).

Then, 980.5 as M+ of this compound was confirmed by MALDI-TOF MS (Matrix Assisted Laser Desorption/Ionization-Time of Flight Mass Spectroscopy).

Further, the structure of this compound was confirmed by NMR measurement.

$^1$H-NMR (CDCl$_3$, 500 MHz) σ(ppm): 7.72 (d, 1H), 7.66-7.48 (m, 18H), 7.43-7.26 (m, 9H), 6.30-6.18 (m, 4H), 1.37 (s, 36H)

Example 6

Synthesis of Exemplified Compound No. C-12

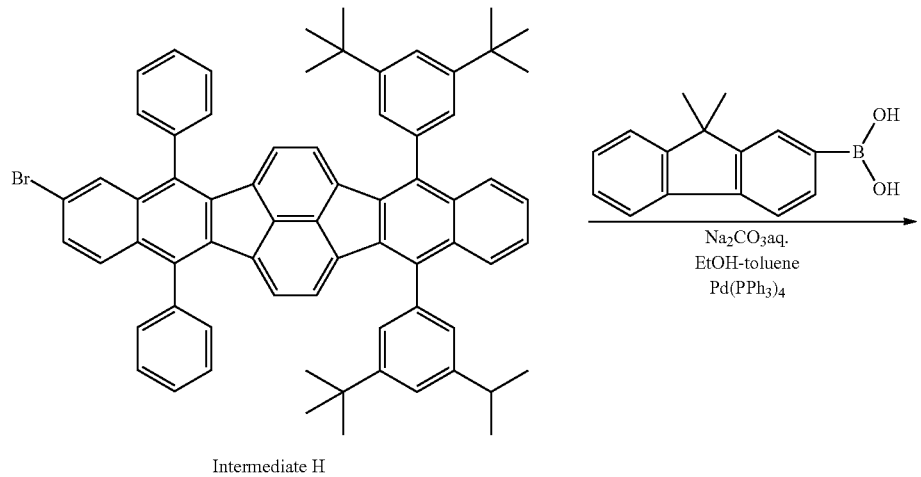

Intermediate H

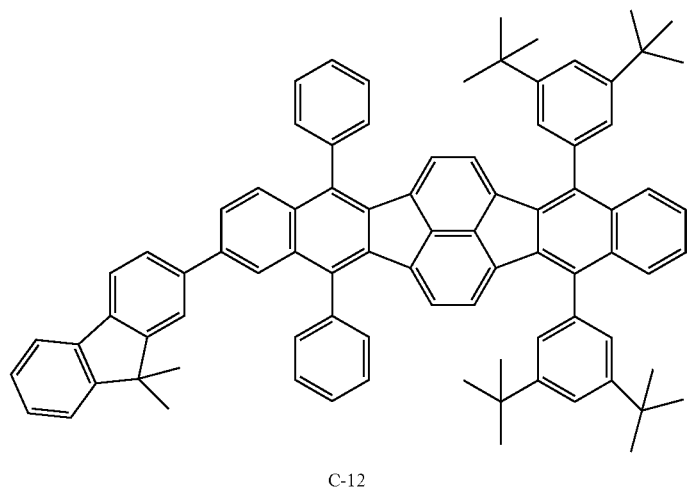

C-12

The following reagents and solvents were charged into a reaction vessel.

Intermediate H, 2.5 g (2.54 mmol)
9,9-dimethylfluoren-2-ylboronic acid: 907 mg (3.81 mmol)
Tetrakis(triphenylphosphine)palladium(0): 5.7 mg (0.05 mmol)
Toluene: 20 mL
Ethanol: 10 mL
2M-Sodium carbonate aqueous solution: 20 mL The reaction solution was heated and stirred for 8 hours in an oil bath at 80° C. Next, after the temperature of the reaction solution was returned to room temperature and the reaction solution was extracted with toluene, the organic layer was washed with water and dried over magnesium sulfate, and then evaporated to dryness under reduced pressure. The organic layer was purified by silica gel column chromatography (eluting solution:hexane/toluene=15:1). The obtained yellowish orange crystal was vacuum dried and then subjected to sublimation purification to thereby obtain 1.8 g of Exemplified Compound No. C-12 (yield: 64.5%).

Then, 1096.6 as M+ of this compound was confirmed by MALDI-TOF MS (Matrix Assisted Laser Desorption/Ionization-Time of Flight Mass Spectroscopy).

Further, the structure of this compound was confirmed by NMR measurement.

$^1$H-NMR (CDCl$_3$, 500 MHz) σ(ppm): 7.72 (d, 1H), 7.75-7.67 (m, 2H), 7.66-7.10 (m, 27H), 6.30-6.18 (m, 4H), 1.47 (s, 6H), 1.38 (s, 36H)

Comparative Example

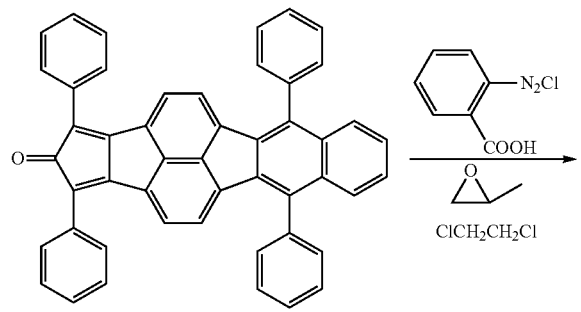

Intermediate E

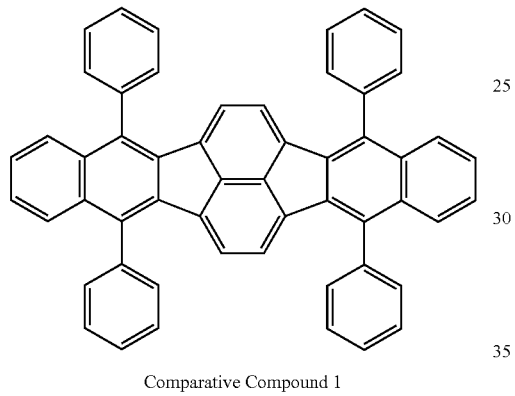

Comparative Compound 1

The following reagents and solvents were charged into a reaction vessel.

Intermediate E: 2.0 g (3.2 mmol)

1,2-Dichloroethane: 30 mL

Benzenediazonium-2-carboxylate hydride: 0.8 g (4.2 mmol)

Propylene oxide: 0.75 g (13 mmol)

Next, the reaction solution was heated and stirred in an oil bath at 80° for 1 hour. After the temperature of the reaction solution was returned to room temperature, the solvent was evaporated under reduced pressure and the residue was purified by silica gel column chromatography (developing solvent: chloroform) to thereby obtain an orange crystal. The obtained crystal was vacuum dried and then subjected to sublimation purification to thereby obtain 231 mg of Comparative Compound 1 (0.34 mmol, yield 11%).

Then, 680.3 as M+ of this compound was confirmed by MALDI-TOF MS (Matrix Assisted Laser Desorption/Ionization-Time of Flight Mass Spectroscopy).

Further, the structure of this compound was confirmed by NMR measurement.

$^1$H-NMR (CDCl$_3$, 600 MHz)σ(ppm): 7.62-7.57 (m, 12H), 7.51 (m, 12H), 7.31 (m, 4H), 6.30 (s, 4H)

As described above, the crystal obtained in Comparative Example 1 was orange, and on the other hand, the crystal obtained in each of Examples 1 to 4 was yellow or yellowish orange. Therefore, it is considered that the compound obtained in each of Examples 1 to 4 has suppressed crystallinity and is a material which is difficult to cause concentration quenching.

Example 7

Production of Organic Light-emitting Device

On a glass substrate, indium tin oxide (ITO) was formed into a film in a thickness of 120 nm as an anode 2 by a sputtering method. Next, the glass substrate having the ITO film formed thereon was ultrasonically cleaned sequentially with acetone and isopropyl alcohol (IPA), subsequently washed with boiled IPA, then dried, and further cleaned with UV/ozone. The glass substrate thus treated was used as a transparent conductive support substrate.

Next, as a hole-transporting layer, a film was formed in a thickness of 20 nm on the transparent conductive support substrate by spin coating of a solution of Compound 1 represented by the following formula in chloroform.

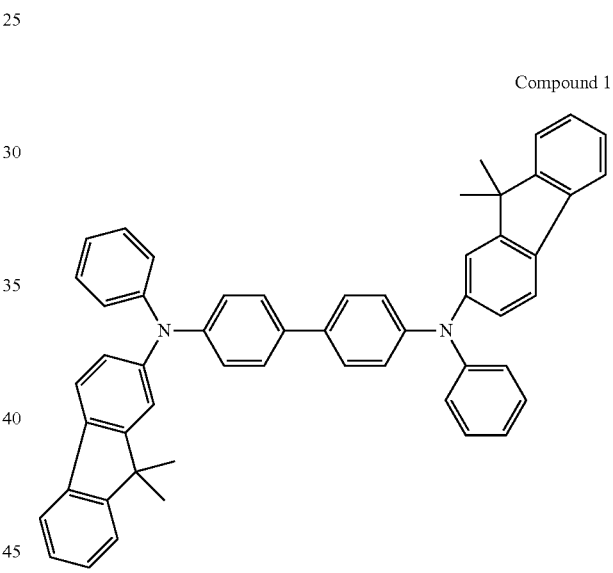

Compound 1

Further, other organic layers and an electrode layer serving as a cathode were successively formed by vacuum evaporation using resistive heating in a vacuum chamber at an inner pressure of 10$^{-5}$ Pa to produce an organic light-emitting device. To be specific, first, as a light-emitting layer, a film was formed in a thickness of 30 nm by coevaporation of Exemplified Compound No. A-2 as a guest and Compound 2 represented by the following formula as a host in such a manner that the content of Exemplified Compound No. A-2 was 5 wt % of the entirety of the light-emitting layer. Next, as an electron-transporting layer, a film of Compound 3 represented by the following formula was formed in a thickness of 40 nm. Then, as a first metal electrode layer, a film of LiF was formed in a thickness of 0.5 nm. Finally, as a second metal electrode layer, a film of Al was formed in a thickness of 150 nm.

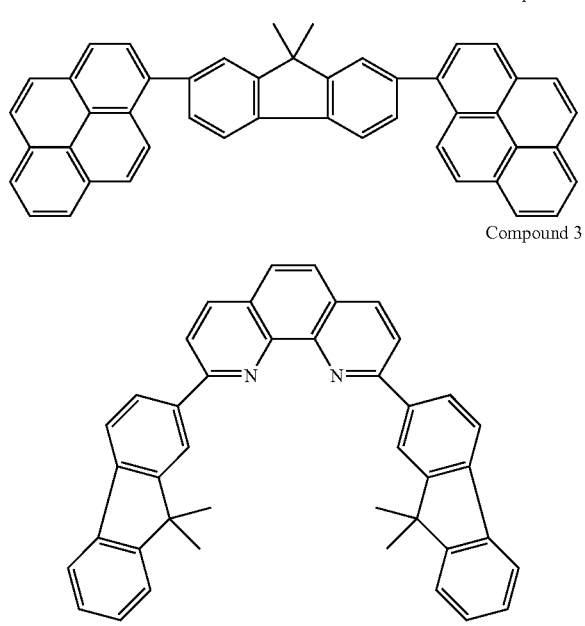

The characteristics of the thus produced organic light-emitting device were examined. Specifically, the current-voltage characteristics of the device were measured with a pico-amp meter (Hewlett Packard 4140B), and the emission luminance of the device was measured with a BM7 manufactured by TOPCON CORPORATION. As a result, the device of this example was observed to emit green light with an emission luminance of 2,000 cd/m$^2$ at an applied voltage of 6.0 V. Further, when a voltage was applied to the device in a nitrogen atmosphere at a current density of 30 mA/cm$^2$ for 100 hours, the luminance was reduced from about 3,100 cd/m$^2$ at an initial stage to about 3,000 cd/m$^2$ after the elapse of the 100 hours, which meant that the luminance degradation was small. In addition, the device was observed to emit green light of good color purity with CIE chromaticity coordinates of x=0.34 and y=0.60.

Example 8

A device was produced by following the same procedure as in Example 7 with the exception that Exemplified Compound No. A-11 was used instead of Exemplified Compound No. A-2 as a guest for the light-emitting layer. The device of this example was observed to emit green light with an emission luminance of 1,900 cd/m$^2$ at an applied voltage of 6.0 V. Further, when a voltage was applied to the device in a nitrogen atmosphere at a current density of 30 mA/cm$^2$ for 100 hours, the luminance was reduced from about 3,000 cd/m$^2$ at an initial stage to about 2,900 cd/m$^2$ after the elapse of the 100 hours, which meant that the luminance degradation was small. In addition, the device was observed to emit green light of good color purity with CIE chromaticity coordinates of x=0.35 and y=0.60.

Example 9

A device was produced by following the same procedure as in Example 7 with the exception that Exemplified Compound No. B-20 was used instead of Exemplified Compound No. A-2 as a guest for the light-emitting layer. The device of this example was observed to emit green light with an emission luminance of 2,400 cd/m$^2$ at an applied voltage of 6.0 V. Further, when a voltage was applied to the device in a nitrogen atmosphere at a current density of 30 mA/cm$^2$ for 100 hours, the luminance was reduced from about 3,700 cd/m$^2$ at an initial stage to about 3,550 cd/m$^2$ after the elapse of the 100 hours, which meant that the luminance degradation was small. In addition, the device was observed to emit green light of good color purity with CIE chromaticity coordinates of x=0.30 and y=0.65.

Example 10

A device was produced by following the same procedure as in Example 7 with the exception that Exemplified Compound No. B-1 was used instead of Exemplified Compound No. A-2 as a guest for the light-emitting layer. The device of this example was observed to emit green light with an emission luminance of 2,200 cd/m$^2$ at an applied voltage of 6.0 V. Further, when a voltage was applied to the device in a nitrogen atmosphere at a current density of 30 mA/cm$^2$ for 100 hours, the luminance was reduced from about 3,500 cd/m$^2$ at an initial stage to about 3,400 cd/m$^2$ after the elapse of the 100 hours, which meant that the luminance degradation was small. In addition, the device was observed to emit green light of good color purity with CIE chromaticity coordinates of x=0.30 and y=0.65.

Example 11

An electrode as an anode and a hole-transporting layer were formed on a substrate by following the same procedure as in Example 7.

Further, the following organic layers and electrode layer serving as a cathode were successively formed by vacuum evaporation using resistive heating in a vacuum chamber at an inner pressure of 10$^{-5}$ Pa to produce an organic light-emitting device.

Light-emitting layer (thickness: 30 nm) using Exemplified Compound A-2 (2 wt %) and Compound 2
Electron-transporting layer (thickness: 40 nm) using Compound 3
Metal electrode layer 1 (thickness: 0.5 nm) using LiF
Metal electrode layer 2 (thickness: 150 nm) using Al The device of this example was observed to emit green light with an emission luminance of 4,300 cd/m$^2$ at an applied voltage of 6.0 V. Further, when a voltage was applied to the device in a nitrogen atmosphere at a current density of 30 mA/cm$^2$ for 100 hours, the luminance was reduced from about 17,000 cd/m$^2$ at an initial stage to about 16,700 cd/m$^2$ after the elapse of the 100 hours, which meant that the luminance degradation was small. In addition, the device was observed to emit green light of good color purity with CIE chromaticity coordinates of x=0.30 and y=0.64.

Example 12

A device was produced by following the same procedure as in Example 11 with the exception that Exemplified Compound No. C-11 was used instead of Exemplified Compound No. A-2 as a guest for the light-emitting layer. The device of this example was observed to emit green light with an emission luminance of 4,500 cd/m$^2$ at an applied voltage of 6.0 V. Further, when a voltage was applied to the device in a nitrogen atmosphere at a current density of 30 mA/cm$^2$ for 100 hours, the luminance was reduced from about 18,500 cd/m$^2$ at an initial stage to about 18,200 cd/m$^2$ after the elapse of the 100 hours, which meant that the luminance degradation was small. In addition, the device was observed to emit green light of good color purity with CIE chromaticity coordinates of x=0.32 and y=0.64.

The present invention is not limited to the above embodiments and various changes and modifications can be made within the spirit and scope of the present invention. Therefore to apprise the public of the scope of the present invention, the following claims are made.

This application claims priorities from Japanese Patent Applications No. 2007-060609, filed Mar. 9, 2007, and No. 2008-023231, filed Feb. 1, 2008, which are hereby incorporated by reference herein.

The invention claimed is:

1. A fused ring aromatic compound represented by the general formula (I):

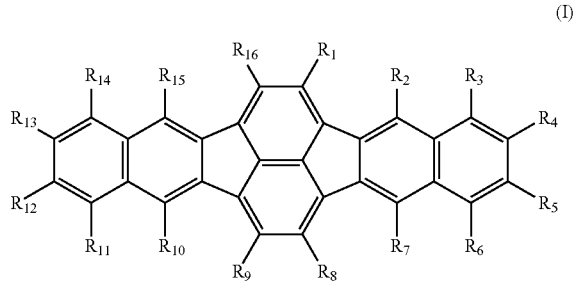

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ each represent, independently of one another, a hydrogen atom, an alkyl group, a substituted or unsubstituted aralkyl group, a substituted or unsubstituted aryl group, a substituted or unsubstituted heterocyclic group, a substituted amino group, or a halogen atom, provided that combinations of $R_2$ and $R_{10}$, and $R_7$ and $R_{15}$ are combinations of different substituents, and combinations of $R_2$ and $R_7$, and $R_{10}$ and $R_{15}$ are combinations of identical substituents, or that combinations of $R_2$ and $R_{10}$, and $R_7$ and $R_{15}$ are combinations of different substituents, and combinations of $R_2$ and $R_{15}$, and $R_7$ and $R_{10}$ are combinations of identical substituents, and wherein $R_3$ and $R_{11}$, $R_4$ and $R_{12}$, $R_5$ and $R_{13}$, and $R_6$ and $R_{14}$, are combinations of identical substituents, and at least one pair of $R_3$ and $R_{11}$, $R_4$ and $R_{12}$, $R_5$ and $R_{13}$, and $R_6$ and $R_{14}$ is not hydrogen.

2. The fused ring aromatic compound according to claim 1, wherein $R_2$, $R_7$, $R_{10}$, and $R_{15}$ each represent a substituted or unsubstituted aryl group.

3. An organic light-emitting device comprising:
an anode;
a cathode; and
a layer comprising an organic compound interposed between the anode and the cathode,
wherein the layer comprises the fused ring aromatic compound set forth in claim 1.

4. The organic light-emitting device according to claim 3, wherein the layer is a light-emitting layer.

5. The organic light-emitting device according to claim 4, wherein the light-emitting layer comprises a host and a guest, and wherein the guest comprises the fused ring aromatic compound.

6. The organic light-emitting device according to claim 3, which is an electroluminescent device that emits light by applying a voltage between the anode and the cathode.

7. An apparatus comprising the organic light-emitting device according to claim 3 and a substrate, the apparatus comprising a color filter.

* * * * *